United States Patent
Karimian Azari et al.

(10) Patent No.: US 12,370,230 B2
(45) Date of Patent: Jul. 29, 2025

(54) HEMP AND PEA FORMULATION AND ITS USE

(71) Applicant: METAGENICS, INC., Aliso Viejo, CA (US)

(72) Inventors: Elnaz Karimian Azari, Aliso Viejo, CA (US); Annalouise O'Connor, Aliso Viejo, CA (US); Nikhat Contractor, Aliso Viejo, CA (US)

(73) Assignee: METAGENICS LLC, Aliso Viejo, CA (US)

( * ) Notice: Subject to any disclaimer, the term of this patent is extended or adjusted under 35 U.S.C. 154(b) by 838 days.

(21) Appl. No.: 17/502,531

(22) Filed: Oct. 15, 2021

(65) Prior Publication Data

US 2022/0031782 A1 Feb. 3, 2022

Related U.S. Application Data

(63) Continuation-in-part of application No. PCT/US2020/028081, filed on Apr. 14, 2020.

(60) Provisional application No. 62/834,325, filed on Apr. 15, 2019.

(51) Int. Cl.
| | | |
|---|---|---|
| A61K 36/185 | (2006.01) | |
| A61K 31/015 | (2006.01) | |
| A61K 31/05 | (2006.01) | |
| A61K 31/164 | (2006.01) | |
| A61P 25/04 | (2006.01) | |
| A61P 39/00 | (2006.01) | |

(52) U.S. Cl.
CPC .......... *A61K 36/185* (2013.01); *A61K 31/015* (2013.01); *A61K 31/05* (2013.01); *A61K 31/164* (2013.01); *A61P 25/04* (2018.01); *A61P 39/00* (2018.01)

(58) Field of Classification Search
None
See application file for complete search history.

(56) References Cited

U.S. PATENT DOCUMENTS

| | | |
|---|---|---|
| 2017/0224645 A1 | 8/2017 | Migliaccio et al. |
| 2020/0000765 A1 | 1/2020 | Borok |
| 2020/0289459 A1 | 9/2020 | Geiling et al. |

FOREIGN PATENT DOCUMENTS

| | | |
|---|---|---|
| EP | 3417846 A1 | 12/2018 |
| WO | 1994012466 A1 | 6/1994 |
| WO | 2015068052 A2 | 5/2015 |
| WO | 2016174661 A1 | 11/2016 |
| WO | 2018157202 A1 | 9/2018 |
| WO | 2019136351 A1 | 7/2019 |

OTHER PUBLICATIONS

Hesselink et al., Therapeutic utility of palmitoylethanolamide in the treatment of neuropathic pain associated with various pathological conditions: a case series, 2012, J Pain Research, 5: 437-442.*
International Search Report for PCT/US2020/028081 dated Aug. 3, 2020, 3 pages.
Cary Leizer BA, David Ribnicky PhD, Alexander Poulev PhD, Slavik Dushenkov PhD & Ilya Raskin PhD (2000) The Composition of Hemp Seed Oil and Its Potential as an Important Source of Nutrition, Journal of Nutraceuticals, Functional & Medical Foods, 2:4, 35-53.
Fine PG, Rosenfeld MJ. The endocannabinoid system, cannabinoids, and pain. Rambam Maimonides Med J. Oct. 29, 2013;4(4):e0022.
Petrosino S, Di Marzo V. The pharmacology of palmitoylethanolamide and first data on the therapeutic efficacy of some of its new formulations. Br J Pharmacol. Jun. 2017;174(11):1349-1365.
Russo EB. Clinical Endocannabinoid Deficiency Reconsidered: Current Research Supports the Theory in Migraine, Fibromyalgia, Irritable Bowel, and Other Treatment-Resistant Syndromes. Cannabis Cannabinoid Res. Jul. 1, 2016;1(1):154-165.
Gabrielsson L, Mattsson S, Fowler CJ. Palmitoylethanolamide for the treatment of pain: pharmacokinetics, safety and efficacy. Br J Clin Pharmacol. Oct. 2016;82(4):932-42.
Petrosino S, Schiano Moriello A, Cerrato S, Fusco M, Puigdemont A, De Petrocellis L, Di Marzo V. The anti-inflammatory mediator palmitoylethanolamide enhances the levels of 2-arachidonoyl-glycerol and potentiates its actions at TRPV1 cation channels. Br J Pharmacol. Apr. 2016,173(7):1154-62.
Russo EB. Taming THC: potential cannabis synergy and phytocannabinoid-terpenoid entourage effects. Br J Pharmacol. Aug. 2011;163(7):1344-64.
Di Marzo V, Piscitelli F. The Endocannabinoid System and its Modulation by Phytocannabinoids. Neurotherapeutics. Oct. 2015;12(4):692-8.
Leweke FM, Piomelli D, Pahlisch F, Muhl D, Gerth CW, Hoyer C, Klosterkotter J, Hellmich M, Koethe D. Cannabidiol enhances anandamide signaling and alleviates psychotic symptoms of schizophrenia. Transl Psychiatry. Mar. 20, 2012;2(3):e94.
Zgair A, Wong JC, Lee JB, Mistry J, Sivak O, Wasan KM, Hennig IM, Barrett DA, Constantinescu CS, Fischer PM, Gershkovich P. Dietary fats and pharmaceutical lipid excipients increase systemic exposure to orally administered cannabis and cannabis-based medicines. Am J Transl Res. Aug. 15, 2016;8(8):3448-59.
Donvito G, Nass SR, Wilkerson JL, Curry ZA, Schurman LD, Kinsey SG, Lichtman AH. The Endogenous Cannabinoid System: a Budding Source of Targets for Treating Inflammatory and Neuropathic Pain. Neuropsychopharmacology. Jan. 2018;43(1):52-79.

(Continued)

*Primary Examiner* — Terry A McKelvey
*Assistant Examiner* — Catheryne Chen
(74) *Attorney, Agent, or Firm* — WARNER NORCROSS + JUDD LLP

(57) ABSTRACT

This disclosure provides a composition comprising a synergistic mixture of hemp oil extract and palmitoylethanolamide (PEA), and a method for suppressing inflammatory and neuropathic pain by administering the composition to a subject. The anti-inflammatory and antinociceptive properties of the composition may be attributed by the entourage effect on the endocannabinoid system. Increasing the levels of endocannabinoids by inhibiting either their degradation or transport from the extracellular space back into the cells is a potential therapeutic target for managing these diseases.

19 Claims, 10 Drawing Sheets

(56) References Cited

OTHER PUBLICATIONS

National Research Council (US) Committee on Recognition and Alleviation of Pain in Laboratory Animals. Recognition and Alleviation of Pain in Laboratory Animals. Washington (DC): National Academies Press (US); 2009. PMID: 20662126.
Medical Outcomes Study 36 Item SF, source: https://www.rand.org/health-care/surveys_tools/mos/36-item-short-form.html.
PROMIS-43 Profile, source: http://www.healthmeasures.net/explore-measurement-systems/promis/intro-to-promis.
Bennett RM, Friend R, Jones KD, Ward R, Han BK, Ross RL. The Revised Fibromyalgia Impact Questionnaire (FIQR): validation and psychometric properties. Arthritis Res Ther. 2009;11(4):R120.
Brief Pain Inventory, source: http://www.npcrc.org/files/news/briefpain_short.pdf.
American Pain Association Quality of Life Scale, source: https://www.theacpa.org/wp-content/uploads/2021/04/ACPA-Quality-of-Life-Scale.pdf.
Orefice NS, Alhouayek M, Carotenuto A, Montella S, Barbato F, Comelli A, Calignano A, Muccioli GG, Orefice G. Oral Palmitoylethanolamide Treatment Is Associated with Reduced Cutaneous Adverse Effects of Interferon-β1a and Circulating Proinflammatory Cytokines in Relapsing-Remitting Multiple Sclerosis. Neurotherapeutics. Apr. 2016;13(2):428-38.
Petrosino, Stefania et al., "2-Pentadecyl-2-Oxazoline, the Oxazoline of Pea, Modulates Carrageenan-Induced Acute Inflammation", Frontiers in Pharmacology, May 2017, vol. 8, Article 308.
Gregory NS, Harris AL, Robinson CR, Dougherty PM, Fuchs PN, Sluka KA. An overview of animal models of pain: disease models and outcome measures. J Pain. Nov. 2013;14(11):1255-69.
Bennett M. The LANSS Pain Scale: the Leeds assessment of neuropathic symptoms and signs. Pain. May 2001;92(1-2):147-57.
Andre, Christelle M et al. "Cannabis sativa: The Plant of the Thousand and One Molecules." Frontiers in plant science vol. 7 19. Feb. 4, 2016.
Arruda, A. M. V. de ; Carregal, R. D. ; Ferreira, R. G., 2000. Apparent digestibility of diets with different starch levels for growing rabbits. Rev. Bras. Zootec., 29 (3): 769-775.
Askari VR, Shafiee-Nick R. The protective effects of beta-caryophyllene on LPS-induced primary microglia M1/M2 Imbalance: a mechanistic evaluation. Life Sci. Feb. 15, 2019;219:40-73.
Astarita G, Piomelli D. Lipidomic analysis of endocannabinoid metabolism in biological samples. J Chromatogr B Analyt Technol Biomed Life Sci. Sep. 15, 2009;877(26):2755-67.
Austin PJ, Moalem-Taylor G. The neuro-immune balance in neuropathic pain: involvement of inflammatory immune cells, immune-like glial cells and cytokines. J Neuroimmunol. Dec. 15, 2010;229(1-2):26-50.
Costa B, Comelli F, Bettoni I, Colleoni M, Giagnoni G. The endogenous fatty acid amide, palmitoylethanolamide, has anti-allodynic and anti-hyperalgesic effects in a murine model of neuropathic pain: involvement of CB(1), TRPV1 and PPARgamma receptors and neurotrophic factors. Pain. Oct. 31, 2008;139(3):541-550.
Bennett GJ, Xie Yk. A peripheral mononeuropathy in rat that produces disorders of pain sensation like those seen in man. Pain. Apr. 1988;33(1):87-107.
Britch SC, Babalonis S, Walsh SL. Cannabidiol: pharmacology and therapeutic targets. Psychopharmacology (Berl). Jan. 2021;238(1):9-28.
Calignano A, La Rana G, Giuffrida A, Piomelli D. Control of pain initiation by endogenous cannabinoids. Nature. Jul. 16, 1998;394(6690):277-81.
Chaplan SR, Bach FW, Pogrel JW, Chung JM, Yaksh TL. Quantitative assessment of tactile allodynia in the rat paw. J Neurosci Methods. Jul. 1994;53(1):55-63.
Corroon J, Phillips JA. A Cross-Sectional Study of Cannabidiol Users. Cannabis Cannabinoid Res. Jul. 1, 2018;3(1):152-161.
Costa B, Trovato AE, Comelli F, Giagnoni G, Colleoni M. The non-psychoactive cannabis constituent cannabidiol is an prally effective therapeutic agent in rat chronic inflammatory and neuropathic pain. Eur J Pharmacol. Feb. 5, 2007;556(1-3):75-83.
Costa B, Colleoni M, Conti S, Parolaro D, Franke C, Trovato AE, Giagnoni G. Oral anti-inflammatory activity of cannabidiol, a non-psychoactive constituent of cannabis, in acute carrageenan-induced inflammation in the rat paw. Naunyn Schmiedebergs Arch Pharmacol. Mar. 2004;369(3):294-9.
Curto-Reyes V, Kirschmann G, Pertin M, Drexler SK, Decosterd I, Suter MR. Neuropathic Pain Phenotype Does Not Involve the NLRP3 Inflammasome and Its End Product Interleukin-13 in the Mice Spared Nerve Injury Model. PLoS One. Jul. 28, 2015.
Di Marzo V, Bifulco M, De Petrocellis L. The endocannabinoid system and its therapeutic exploitation. Nat Rev Drug Discov. Sep. 2004;3(9):771-84.
Duarte DB, Vasko MR, Fehrenbacher JC. Models of inflammation: carrageenan air pouch. Curr Protoc Pharmacol. Mar. 2012;Chapter 5:Unit5.6.
Dubový P, Brazda V, Klusáková I, Hradilová-Svíženská I. Bilateral elevation of interleukin-6 protein and mRNA in both lumbar and cervical dorsal root ganglia following unilateral chronic compression injury of the sciatic nerve. J Neuroinflammation. May 1, 2013;10:55.
Dubuisson D, Dennis SG. The formalin test: a quantitative study of the analgesic effects of morphine, meperidine, and brain stem stimulation in rats and cats. Pain. Dec. 1977;4(2):161-174.
Guida F, Luongo L, Boccella S, Giordano ME, Romano R, Bellini G, Manzo I, Furiano A, Rizzo A, Imperatore R, Iannotti FA, D'Aniello E, Piscitelli F, Sca Rossi F, Cristino L, Di Marzo V, de Novellis V, Maione S. Palmitoylethanolamide induces microglia changes associated with increased migration and phagocytic activity: Involvement of the CB2 receptor. Sci Rep. Mar. 23, 2017;7(1):375.
Iannotti FA, Di Marzo V, Petrosino S. Endocannabinoids and endocannabinoid-related mediators: Targets, metabolism and role in neurological disorders. Prog Lipid Res. Apr. 2016;62:107-28.
Franchi L, Muñoz-Planillo R, Núñez G. Sensing and reacting to microbes through the inflammasomes. Nat Immunol. 2012;13(4):325-332. Published Mar. 19, 2012.
Genaro K, Fabris D, Arantes ALF, Zuardi AW, Crippa JAS, Prado WA. Cannabidiol Is a Potential Therapeutic for the Affective-Motivational Dimension of Incision Pain in Rats. Front Pharmacol. 2017;8:391. Published Jun. 21, 2017. doi:10.3389/fphar.2017.00391.
Hammell, D C et al. "Transdermal cannabidiol reduces inflammation and pain-related behaviours in a rat model of arthritis." European journal of pain (London, England) vol. 20,6 (2016): 936-48.
LoVerme J, Russo R, La Rana G, Fu J, Farthing J, Mattace-Raso G, Meli R, Hohmann A, Calignano A, Piomelli D. Rapid broad-spectrum analgesia through activation of peroxisome proliferator-activated receptor-alpha. J Pharmacol Exp Ther. Dec. 2006;319(3):1051-61.
Mabou Tagne A, Fotio Y, Lin L, Squire E, Ahmed F, Rashid TI, Karimian Azari E, Piomelli D. Palmitoylethanolamide and hemp oil extract exert synergistic anti-nociceptive effects in mouse models of acute and chronic pain. Pharmacol Res. May 2021;167:105545.
Malfait AM, Gallily R, Sumariwalla PF, Malik AS, Andreakos E, Mechoulam R, Feldmann M. The nonpsychoactive cannabis constituent cannabidiol is an oral anti-arthritic therapeutic in murine collagen-induced arthritis. Proc Natl Acad Sci U S A. Aug. 15, 2000,97(17):9561-6.
Varrassi G et al. Towards an effective and safe treatment of inflammatory pain: a delphi-guided expert consensus. Adv Ther. 2019;36(10):2618-2637.
Schuel H et al. N-Acylethanolamines in human reproductive fluids. Chem Phys Lipids. 2002; 121(1-2):211-227.
Lo Verme J et al. The nuclear receptor peroxisome proliferator-activated receptor-alpha mediates the anti-inflammatory actions of palmitoylethanolamide. Mol Pharmacol. 2005;67(1):15-19.
Tagne AM et al. Palmitoylethanolamide and hemp oil extract exert synergistic anti-nociceptive effects in mouse models of acute and chronic pain. Pharmacol Res. 2021:105545.
Coppola, M. et al., "Palmitoylethanolamide: From endogenous cannabimimetic substance to innovative medicine for the treatment of cannabis dependence", Medical Hypotheses 81 (2013) 619-622.

(56) References Cited

OTHER PUBLICATIONS

Rahimi, A. et al., "Interaction between the protective effects of cannabidiol and palmitoylethanolamide in experimental model of multiple sclerosis in C57BL/6 mice", Neuroscience 290 (2015) 279-287.

Murakami K, Elmlund H, Kalisman N, Bushnell DA, Adams CM, Azubel M, Elmlund D, Levi-Kalisman Y, Liu X, Gibbons BJ, Levitt M, Kornberg RD. Architecture of an RNA polymerase II transcription pre-initiation complex. Science. Nov. 8, 2013;342(6159):1238724.

Ren K, Dubner R. Interactions between the immune and nervous systems in pain. Nat Med. Nov. 2010;16(11):1267-76.

Rock, E.M., Limebeer, C.L. & Parker, L.A. Effect of cannabidiolic acid and Δ9-tetrahydrocannabinol on carrageenan-induced hyperalgesia and edema in a rodent model of inflammatory pain. Psychopharmacology 235, 3259-3271 (2018).

Russo, E., Guy, G. and Robson, P. (2007), Cannabis, Pain, and Sleep: Lessons from Therapeutic Clinical Trials of Sativex®, a Cannabis-Based Medicine. Chemistry & Biodiversity, 4: 1729-1743.

Sacerdote P, Niada S, Franchi S, Arrigoni E, Rossi A, Yenagi V, de Girolamo L, Panerai AE, Brini AT. Systemic administration of human adipose-derived stem cells reverts nociceptive hypersensitivity in an experimental model of neuropathy. Stem Cells Dev. Apr. 15, 2013;22(8):1252-63.

Scholz J, Woolf CJ. The neuropathic pain triad: neurons, immune cells and glia. Nat Neurosci. Nov. 2007; 10(11):1361-8.

Simão da Silva KAB, Paszcuk AF, Passos GF, Silva ES, Bento AF, Meotti FC, Calixto JB. Activation of cannabinoid receptors by the pentacyclic triterpene α,β-amyrin inhibits inflammatory and neuropathic persistent pain in mice. Pain. Aug. 2011;152(8):1872-1887.

Thacker MA, Clark AK, Marchand F, McMahon SB. Pathophysiology of peripheral neuropathic pain: immune cells and molecules. Anesth Analg. Sep. 2007;105(3):838-47.

Ward E, DeSantis C, Robbins A, Kohler B, Jemal A. Childhood and adolescent cancer statistics, 2014. CA Cancer J Clin. Mar.-Apr. 2014;64(2):83-103.

Williams AC, Barry BW. Penetration enhancers. Adv Drug Deliv Rev. Mar. 27, 2004;56(5):603-18.

Wise LE, Cannavacciuolo R, Cravatt BF, Martin BF, Lichtman AH. Evaluation of fatty acid amides in the carrageenan-induced paw edema model. Neuropharmacology. Jan. 2008;54(1):181-8.

Xiong W, Cui T, Cheng K, Yang F, Chen SR, Willenbring D, Guan Y, Pan HL, Ren K, Xu Y, Zhang L. Cannabinoids suppress inflammatory and neuropathic pain by targeting α3 glycine receptors. J Exp Med. Jun. 4, 2012;209(6):1121-34.

Zhu YF, Linher-Melville K, Niazmand MJ, Sharma M, Shahid A, Zhu KL, Parzei N, Sidhu J, Haj C, Mechoulam R, Singh G. An evaluation of the anti-hyperalgesic effects of cannabidiolic acid-methyl ester in a preclinical model of peripheral neuropathic pain. Br J Pharmacol. Jun. 2020;177(12):2712-2725.

Lin L, Yang H, Jones PJ. Quantitative analysis of multiple fatty acid ethanolamides using ultra-performance liquid chromatography-tandem mass spectrometry. Prostaglandins Leukot Essent Fatty Acids. Dec. 2012;87(6):189-95.

\* cited by examiner

HEMP AND PEA FORMULATION AND ITS USE

CROSS-REFERENCE TO RELATED APPLICATIONS

This application is a continuation-in-part application of International Application No. PCT/US2020/028081 filed on 14 Apr. 2020, which claims priority to and all advantages of U.S. Prov. Appl. No. 62/834,325 filed on 15 Apr. 2019, the contents of which are hereby incorporated by reference.

FIELD OF THE INVENTION

The present invention relates generally to compositions and methods for suppressing inflammatory and neuropathic pain and, more specifically, to a composition comprising palmitoylethanolamide (PEA) and a hemp oil and related methods and uses of the composition.

BACKGROUND OF THE INVENTION

The endocannabinoid system (ECS) is a lipid signaling system involved in many aspects of vertebrate physiology including modulation of pain and inflammation. This system is able to downregulate stress-related signals that lead to chronic inflammation and certain types of pain (e.g., see Fine P. G. et al. Rambam Maimonides Med J. 2013 October; 4(4): e0022). Stress is mostly defined as any stimulus that presents a challenge to homeostasis—typically a real or perceived threat to an organism's wellbeing. ECS consists of receptors, endogenous ligands (known as endocannabinoids), and the ligand metabolic enzymes. The two major endocannabinoids, anandamide (AEA) and 2-arachidonolyglycerol (2-AG) bind with different affinities to cannabinoid receptor type 1 (CB1) and type 2 (CB2) located throughout the body, and their biological function is terminated by hydrolyzing enzymes fatty acid amide hydrolase (FAAH) and monoacylglycerol lipase (MAGL), respectively (e.g., see Di Marzo V et al. Nat Rev Drug Discov. 2004; 3(9):771-784). The classic ECS has extended with the discovery of other receptors such as the peroxisome proliferator-activated receptors (PPARs), and the endocannabinoid-like mediators such as palmitoylethanolamide (PEA). PEA, the ethanolamide of palmitic acid, classifies as an endocannabinoid-like molecule because it is synthesized and metabolized by the same class of enzymes as AEA. However, PEA only in part shares the same mechanism of action. PEA is known to exert anti-inflammatory properties, as well as neuroprotective and antinociceptive effects (e.g., see Petrosino S. et al. British Journal of Pharmacology (2017) 174 1349-1365 ("Petrosino 2017")).

Various pathological states are associated with suboptimal functioning of ECS as a result of the altered levels of the endocannabinoids, their metabolizing enzymes, and the relative abundance of cannabinoid receptors (e.g., see Russo; Cannabis and Cannabinoid Research 2016, 1.1 ("Russo 2016")). Alzheimer's disease, Parkinson's disease, Huntington's disease, multiple sclerosis, and epilepsy are examples of neurological disorders in which the ECS function is altered (e.g., see F. A. Iannotti et al. Progress in Lipid Research 62 (2016) 107-128 ("Iannotti 2016"). In addition, clinical endocannabinoid deficiency was suggested as the etiology of certain conditions such as migraine, irritable bowel syndrome, fibromyalgia, and related conditions. For example, it has been shown that suboptimal functioning of ECS in the spinal cord was associated with increased pain sensitivity (e.g., see Russo 2016). Thus, maintaining healthy levels of ECS is necessary for optimal health.

Because of the importance of the ECS to overall health outcomes, supporting the appropriate functioning of the ECS could be a relevant therapeutic goal. Several synthetic modulators of ECS have been used and studied for a broad range of diseases; however, they have introduced serious unexpected complexities. Therefore, there is an ongoing need for identifying methods of enhancing the ECS to treat or ameliorate the symptoms of these diseases without drugs or medical procedures. Nutritional therapy with naturally occurring cannabinoids found in foods such as PEA, as well as plant-derived cannabinoids also known as 'phytocannabinoids' in combination with other bioactive compounds within broad-spectrum hemp oil such as terpenes appear to be promising candidates due to their high safety and low adverse effects profiles.

PEA is naturally produced in many plants and foods like egg yolk, peanut oil or soybean lecithin, as well as in different tissues, cells and body fluids (e.g., see Petrosino 2017; and Gabrielsson L. et al. Br J Clin Pharmacol (2016) 82 932-942). In the body, PEA, like endocannabinoids, is produced on demand from membrane phospholipids and its concentrations alters during several pathological conditions, such as pain and inflammation, indicating its function as body's self-repairing mechanism (e.g., see Iannotti 2016). PEA can act via multiple mechanisms: A) the 'Autacoid Local Inflammation Antagonism (ALIA)' to down-regulate mast cell activation; B) the 'direct receptor-mediated mechanism' via activation of at least two different receptors: the PPAR-α and the GPCR 55 (GPR55); and C) the 'entourage effect' by increasing the effects of endocannabinoids (e.g., see Iannotti 2016; and Petrosino 2017). The latter mechanism of action is based on the capability of PEA in inhibiting the expression or activity of FAAH, and therefore, increasing the levels of AEA and 2-AG, which activate both CB receptors and the transient receptor potential vanilloid receptor type 1 (TRPV1) channels. In addition, PEA can potentiate the AEA- or 2-AG-induced TRPV1 activation and desensitization, contributing to its anti-inflammatory or analgesic effects (e.g., see Petrosino S. et al. Br J Pharmacol. 2016 April; 173(7):1154-62). Another possible mechanism to its entourage effects is related to the indirect action of PEA on upregulating CB2 receptors expression mediated by PPAR-α (e.g., see F. Guida, et al. Sci Rep. 2017; 7: 375).

Phytocannabinoids modulate a variety of physiological systems influenced by the ECS as well as support the overall functioning of the ECS. Broad-spectrum hemp extract is sourced from aerial plant parts of industrial hemp (stalk, stems, seed and flower) that contain beneficial phytocannabinoids such as cannabidiol (CBD) and cannabigerol (CBG), and terpenes such as β-Caryophyllene (BCP). Terpenes are fragrant oils common to human diets and share a precursor with phytocannabinoids (e.g., see Russo E. Br J Pharmacol. 2011 August; 163(7): 1344-1364). Phytocannabinoids within hemp oil have specific and complementary effect on the ECS either by interacting directly with CB1 and CB2 receptors or inhibiting enzymes that are involved in breaking down endocannabinoids (e.g., see DiMarzo V. et al. Neurotherapeutics (2015) 12:692-698). For example, CBD exert anti-inflammatory activity by suppressing FAAH activity, thereby increasing concentrations of the anti-inflammatory endocannabinoid AEA (e.g., see Leweke F M, et al. Transl Psychiatry. 2012; 2:e94). Also, BCP, one of the known terpenes found in many plants and spices such as pepper and cloves, exerts anti-inflammatory and antioxidant effects through activation of the CB2 receptor (e.g., see Askari V R, et al. Life Sci. 2019 Feb. 15; 219:40-73). A synergy not only between phytocannabinoids, but also their interactions with terpenoid compounds in hemp extract determine its entourage effect on ECS and therefore, its therapeutic potential.

Because the entourage effect is not clearly understood, the field of cannabinoid research continues to seek combinations that would provide desired and enhanced effects in therapy, especially human therapy.

BRIEF SUMMARY OF THE INVENTION

An objective of the present invention is to provide a method for preventing or ameliorating inflammatory and neuropathic pain and associated diseases. As such, a composition comprising palmitoylethanolamide (PEA) and a hemp oil is provided. It has been surprisingly found that the combination of PEA and hemp oil extract is synergistic as a therapeutic strategy for reducing the inflammation and pain, improving quality of life and rebalancing the ECS.

In some embodiments, the composition is formulated as an oral composition. The oral composition is adapted for oral administration to a subject, and may comprise a softgel or capsule shell encapsulating the combination of the PEA and the hemp oil, i.e., such that the oral composition is formulated as a softgel or capsule.

In addition, the present invention provides proof of principle that synergistic actions of the composition on ECS represent a desirable strategy for pain and inflammation reduction. As such, a method of ameliorating a condition associated with pain, inflammation, stress, and/or neuropathy of a subject is also provided, and comprises administering to the subject an effective amount of the composition These and other objects, advantages, and features of the invention will be more fully understood and appreciated by reference to the description of the embodiments and examples set forth herein.

BRIEF DESCRIPTION OF DRAWINGS

Other advantages of the present invention will be readily appreciated, as the same becomes better understood by reference to the following detailed description when considered in connection with the accompanying drawings wherein.

Data are expressed as mean±S.E.M. (n=3-5 per group) and analyzed by one-way ANOVA (AUC curves) and two-way ANOVA (concentration-time curves) followed by Dunnett's test for multiple comparisons. **P<0.01 vs. baseline or combination of HOE plus PEA.

Figure 9:
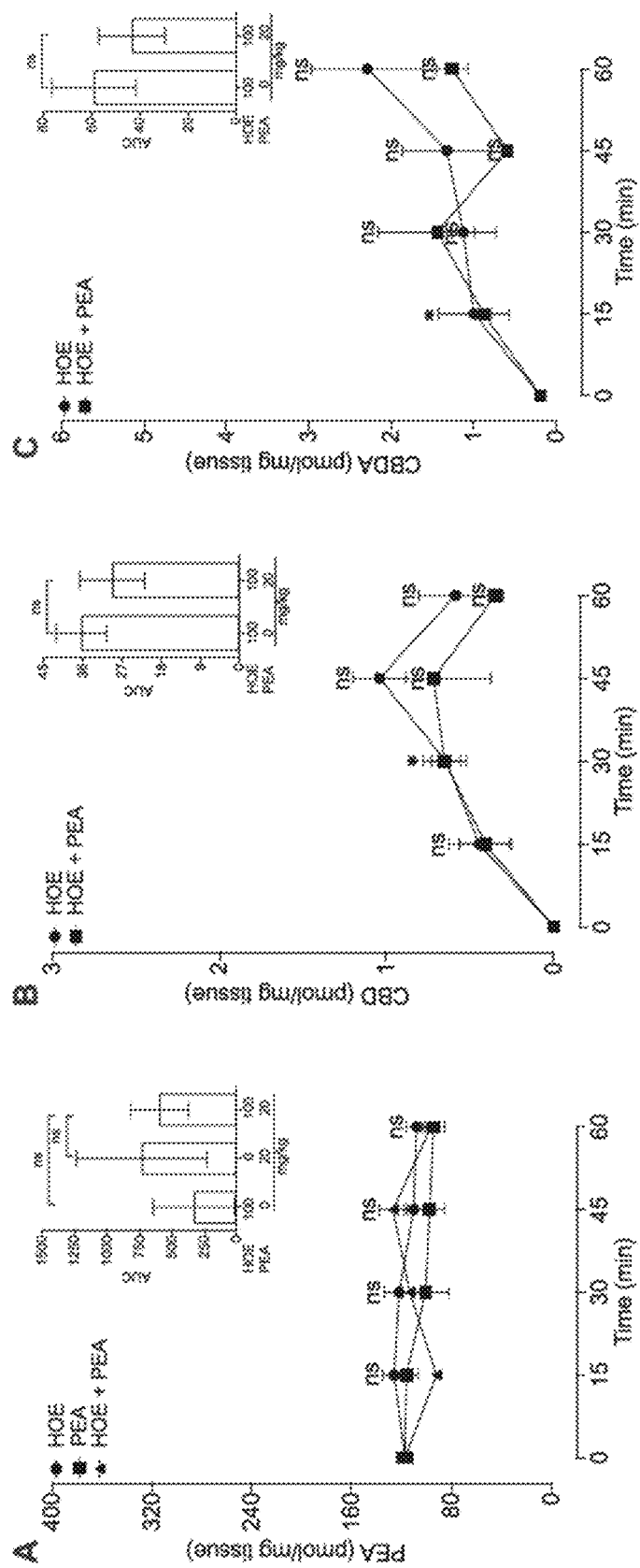

FIG. 9. illustrates concentration-time curves and overall drug exposure (AUC) for PEA (A), CBD (B) and CBDA (C) in lumbar spinal cord tissue, after oral administration of HOE (100 mg·kg-1) alone or in combination with PEA (20 mg·kg-1). Data are expressed as mean±S.E.M. (n=3-5 per group) and analyzed by one-way ANOVA (AUC curves) and two-way ANOVA (concentration-time curves) followed by Dunnett's test for multiple comparisons. *P<0.05 vs. baseline or combination of HOE plus PEA.

Figure 10:
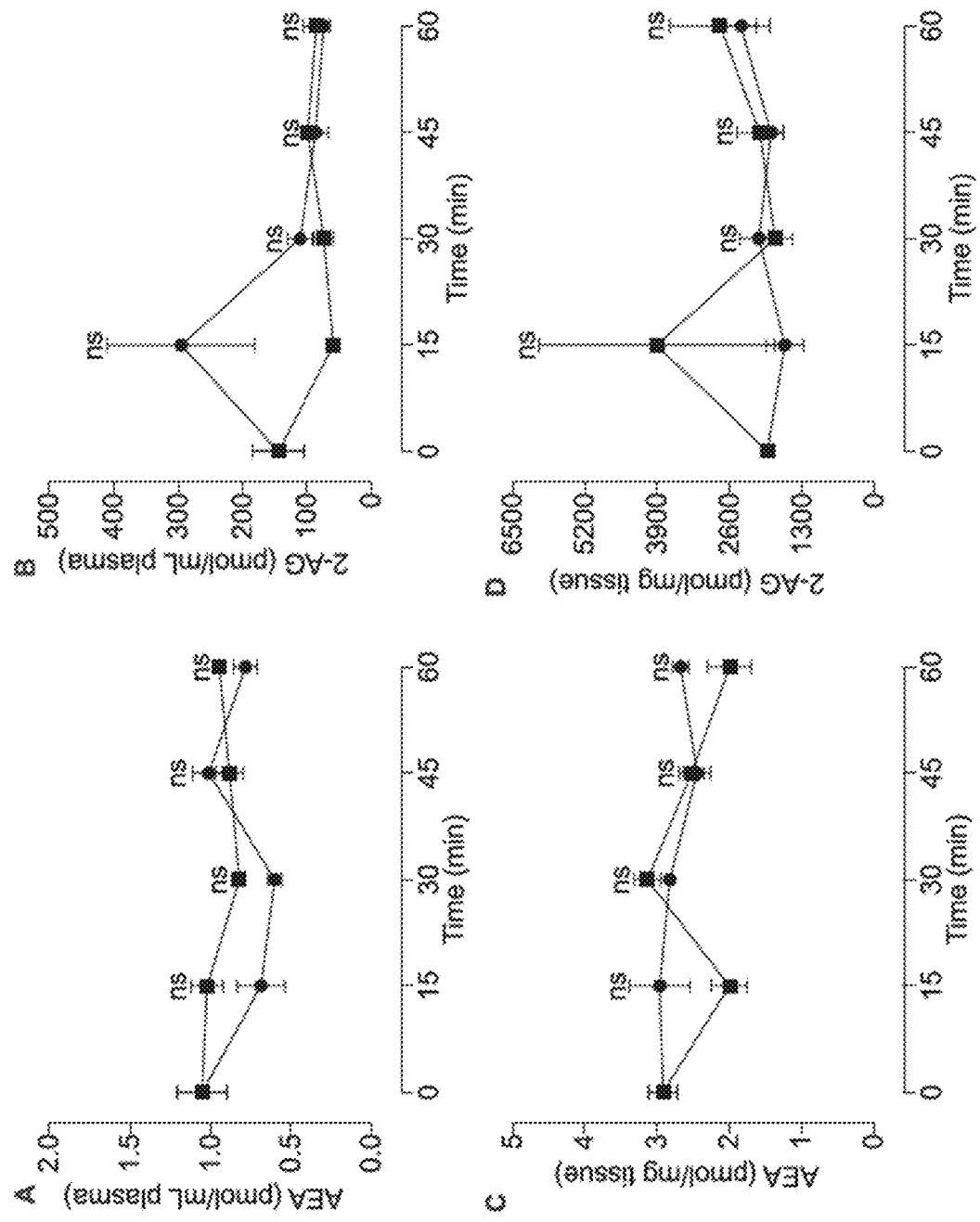

FIG. 10. illustrates time-course of the effects of oral administration of HOE (100 mg·kg-1; •) alone or in combination with PEA (20 mg·kg-1; ■) on the levels of anandamide (AEA) and 2-arachidonoyl-sn-glycerol (2-AG) in mouse plasma (Upper panels) and spinal cords (lower panels). Data are expressed as mean} S.E.M. (n=3-5 per group) and analyzed by twoway ANOVA followed by Dunnett's test for multiple comparisons.

DETAILED DESCRIPTION OF THE INVENTION

A composition for administration to a subject having an endocannabinoid system (ECS) is provided. The composition comprises a synergistic combination of palmitoylethanolamide (PEA) and a hemp oil. The hemp oil may also be referred to as hemp oil extract (HOE).

The composition, which may also be referred to as the "formulation" or the "formula" may optionally contain any number of carrier oils and/or other actives and/or other inactives aside from the PEA and the hemp oil, and the amounts used may vary up to 20% from the amounts described in the examples below. Fatty acids (which are derived in the body from triglycerides, for example), triglycerides or fats can be used, and a number of them are in use, such as coconut oil, Medium chain triglycerides (MCTs), and fat containing foods generally. In various embodiments, long chain fatty acids such as sesame oil, olive oil, hemp seed oil, and omega-3 fatty acids, such as derived from marine organisms, including fish, algae and plants, as well as other seed or nut oils can be used as a carrier oil. The presence of dietary lipids or lipid excipients may increase the oral bioavailability of active ingredients. Without being bound by any specific theory, the increased bioavailability may be due to solubility enhancement, cellular transport, or activation of transport mechanisms within the body (e.g., see Zagir. A. et al. Am J Transl Res 2016; 8(8):3448-3459).

The study that resulted in this invention was designed to examine the effect of nutrition support formulations on pain sensitivity and inflammation in rodents with inflammatory and/or neuropathic pain, and whether correlation existed between disease state and those parameters. In addition, we have conducted studies to assess the impact on subjective assessment of pain, as well as quality of life, were conducted in individuals with chronic inflammatory and/or neuropathic pain.

As used herein, "an effective amount" refers to an amount sufficient for the treatment of diseases at a reasonable benefit/risk ratio applicable to a medical treatment, and the level of the effective dose may be determined from factors including severity of illness, drug activity, age, genetic background, body weight, health conditions, drug sensitivity of a subject, administration time, administration route and dissolution rate, length of treatment of the formulation of the present invention, drug(s) used in combination with or simultaneously with the formulation of the present invention, and other factors well known in the medical field. The formulation of the present invention may be administered in an effective amount. The formulation of the present invention may be administered as an individual therapeutic agent or in combination with other therapeutic agent(s), and also sequentially or simultaneously with the conventional therapeutic agent(s). The formulation of the present invention may be administered as a single dose or in multiple divided doses. Additionally, it is important that the least amount which can achieve the maximum effect without any side effects be administered in consideration of all the factors described above. As used and described herein, the dose of the formulation of the present invention may be determined by a skilled person in the art considering the intended use(s), severity of disease(s), age, body weight, sex and medical history of a subject, or the kinds of ingredients used as active ingredient(s), etc. For example, the formulation of the present invention may be administered in the range of from about 2.5 mg/kg/day to about 40 mg/kg/day for mammals including humans, and optionally from about 5 mg/kg/day to about 30 mg/kg/day. Higher or lower dosages, e.g. 0.1× to 10× of these specific ranges, are also contemplated. Where required, the formulation may be administered in amounts as high as 10 mg/kg/day at the discretion of a skilled practitioner. Other dosages can readily be determined by the skilled practitioner. The formulation of the present invention may be administered once daily or in a few divided doses, although administration is not particularly limited thereto. However, as described herein the method of the invention required the clinician to consider the specific parameters described herein to assure the dosage is optimized.

As described herein the PEA referred to is PEA that is commercially available. Typically, such commercial products used in formulations comprising PEA, have PEA of purity 95%, 98%, or greater. Because of the chemical nature of PEA, solvents may be used in the purification thereof, however, it is preferred that any such solvent be non-toxic, and it is preferred that such solvents be removed before final formulation into a product for human consumption.

Typically, any such PEA products, or formulations containing them have residual solvent, such as isopropanol, limited to not more than 750 ppm. That is the preferred case in certain embodiments of the present invention as well. The skilled person in the art will recognize that this is generally because of the known toxicity of isopropanol and such similar solvents, and consumer's general lack of acceptance of solvents in consumable products.

Typically, the PEA is dispersible in warm or cold water. Such dispersible PEA is available commercially as a powder, where it is formulated specifically to increase gastrointestinal or aqueous solubility as well as bioavailability. Such PEA is useful in the composition due to its ease of handling. For example, combining 90% by weight ratio of PEA with the balance substantially a lipid-based drug delivery system, preferably capable of forming micelles, or dispersing lipids in water (e.g., LIPISPERSE® technology developed by Pharmako Biotechnologies) one may create a mixed micellar transport system that allows for effective delivery of the PEA. Such lipid-based delivery systems typically include oils, such as (for example) coconut oil, lime oil, olive oil or others, and surfactant-like molecules such as polyglycerol polyricinoleate, lecithin (e.g., sunflower and/or oat), and certain vitamins, such as Vitamin E or its esters, such as Vitamin E acetate.

The amount of PEA utilized in the composition may vary, e.g. depending on a desired serving size thereof. In certain embodiments, the composition comprises at least 300 mg PEA per serving of the composition. In particular embodiments, the composition comprises from about 500 to about 700 mg PEA, optionally about 600 mg PEA, per serving of the composition. Higher or lower amounts of PEA, e.g. 0.1× to 10× of these specific ranges/amount, are also contemplated.

While hemp oil is contemplated as an active in the composition of the invention, preferably hemp oils used herein will have significant amounts of phytocannabinoids in the hemp oil itself; or may have phytocannabinoids and terpenes added thereto. In certain embodiments, the hemp oil contains significant or enhanced (i.e., added) amounts of phytocannabinoids. For example, in some embodiments, the hemp oil has a phytocannabinoid profile (for example in 500 mg of the hemp oil) containing levels of phytocannabinoid active components listed in Andre C M, et al Front. Plant Sci. 2016. 7:19, which phytocannabinoids and profiles are incorporated by reference herein.

In certain embodiments, the hemp oil is derived from the "aerial" parts of the plant (i.e., those parts of the plant above the ground, such as flowers, leaves, seeds, buds and stems, but not the root). Where the hemp oil is augmented with phytocannabinoids or terpenes, these may be sourced from other plants. Exemplary sources include oils rich in such compounds, such as clove oil, pepper oil (preferably from the bud or fruit thereof), or the like. For example, in the formulation exemplified below, the hemp oil used provides 3 mg beta caryophyllene, a terpene described above. In certain embodiments, the hemp oil is fortified with a blend of black pepper oil and clove bud oil. In some such embodiments, the composition comprises at least 3.5 mg of such a blend, such as about 7.5 of the blend per serving of the composition. Higher or lower amounts of the blend, e.g. 0.1× to 10× of these specific ranges/amount, are also contemplated.

The amount of the hemp oil utilized in the composition may vary, e.g. depending on a desired serving size thereof. In certain embodiments, the composition comprises at least 70 mg of the hemp oil per serving of the composition, such as an amount of about 140 mg per serving. In other embodiments, the composition comprises at least 250 mg of the hemp oil per serving of the composition, such as an amount of about 500 mg per serving. Higher or lower amounts of the hemp oil, e.g. 0.1× to 10× of these specific ranges/amount, are also contemplated. One of skill in the art will appreciate the variations in formulation in view of the examples below.

The composition may be formulated and used as a liquid or suspension. However, it is preferred for ease of handling that the formulation be encapsulated in a gelcap (preferably of gelatin or similar dissolvable and biologically sensible material, often these may be referred to as "softgels") or otherwise dissolvable capsule, such as cellulose capsules often used for hydrophobic dosage forms, and those dosage forms that may be a hydrophobic liquid. Typically, the formulations and compositions of the invention are prepared in capsules or gel-cap, such as using softgel shells prepared from gelatin, glycerin, and water, and optionally dyes or colorings such as carob extract.

Dosages or formulations of the composition are prepared using methods known in the art. Similarly, the use of capsules or gelcaps used in preparing a dosage for use by consumers and the like is well known in the art, and methods for making the same are apparent and known to those skilled in the art.

The dose of the product ranges from an effective amount, which is typically from about 300 mg to as much as about 1800 mg per day, and may be divided into multiple portions for delivery, such as in the form of the capsules described above and exemplified below. For example, each capsule may comprise any portion of the total serving of the composition, such as an amount of about 50% of the composition to give a serving size of 2 capsules, an amount of about 25% of the composition to give a serving size of 4 capsules, etc. Higher or lower dosages of the product, e.g. 0.1× to 10× of this specific range, are also contemplated.

Typically, the synergistic ratio of the PEA to the phytocannabinoids (e.g. in the hemp oil) is from about 50:1 to about 1.2:1, further formulations have a ratio of about 40:1 to about 30:1, and yet further formulations have a ratio of about 40:1 (PEA:phytocannabinoids). This is generally on a weight basis, e.g. wt./wt. One of skill in the art will appreciate that these ratios differ from the overall ratio of the amounts of the PEA and hemp oil present in the composition (i.e., the weight ratio (wt./wt.)), which is typically from about 1.2:1 to about 4.5:1 (PEA:hemp oil). For example, as will be appreciated from the examples below, in certain embodiments the composition comprises the PEA and the hemp oil in a weight ratio (wt./wt.) of about 1.2:1. In these embodiments, the composition is typically formulated with from about 38% to about 43% by weight of the PEA and from about 31% to about 35% by weight of the hemp oil. In other embodiments, the composition comprises the PEA and the hemp oil in a weight ratio (wt./wt.) of about 4.3:1, optionally of about 4.1:1. In these embodiments, the composition is typically formulated to comprise the PEA in an amount of from 78 to 83 wt. % and the hemp oil in an amount of from 17 to 20 wt. %, each based on the total weight of the composition. Of course, weight loadings may differ from these amounts, such as where excipients are utilized in addition to the synergistic combination described above. Higher or lower amounts, e.g. 0.1× to 10× of these specific ranges, are also contemplated.

Example 1: Composition Formulation, Softgel/Capsules Dosage Forms

An exemplary composition is prepared with the formulation shown in Table 1 below, by combining PEA and a broad-spectrum hemp extract sourced from aerial plant parts of industrial hemp ("Hemp Oil").

TABLE 1

Softgel/Capsules Dosage Formulation 1

| Serving Size: 2 softgels/capsules | Nutrient | Amount Per Softgel (mg) |
|---|---|---|
| | Palmitoylethanolamide (PEA) | 300 |
| | Hemp Oil | 250 |

The composition is then encapsulated. In particular, hard-shell capsules filled with active ingredients and excipients, and then sealed with hard shell caps including typical clear vegetable caps and hydroxypropyl methylcellulose or hypromellose (HPMC). Lubricants such as stearic acid may be used to improve rheological properties of product powders during manufacturing. Such excipients are typically are used in amounts of from about 0.1 to about 50 mg. In an exemplary formulation, about 6.5 mg is used.

Soft Gelatin Capsules (Softgels)

Softgels consist of a gelatin-based shell surrounding a liquid fill. The shells are a combination of gelatin, water, a coloring agent, such as carob, and a plasticizer, such as glycerin. Excipients for softgels, such as olive oil, beeswax, and sunflower lecithin are used to either enhance the solubility of the softgel and to provide a more precise dosing of the active ingredient, or as a coating to the finished softgel to aid in the manufacturing process. The range for olive oil is from about 10 to about 1000 mg, with an exemplary formulation including about 130 mg. The range for beeswax is from about 0.1 to about 100 mg, with an exemplary formulation including about 50 mg. The range for lecithin is from about 0.1 to about 50 mg, with an exemplary formulation including about 20 mg.

Another exemplary composition for use as a dietary supplement is prepared according to the general procedure above with the formulation shown in Table 2 below. In particular, this exemplary composition is prepared by encapsulating a mixture of 300 mg PEA, 70 mg broad-spectrum hemp oil extract sourced from aerial plant parts of industrial hemp, and 3.75 mg of a blend of black pepper oil and clove bud oil to give a softgel. In this formulation, a serving size of 2 softgels/day is utilized.

TABLE 2

Softgel/Capsules Dosage Formulation 2

| Serving Size: 2 softgels/capsules Nutrient | Amount Per Softgel (mg) | Amount Per Serving (mg) |
|---|---|---|
| Palmitoylethanolamide (PEA) | 300 | 600 |
| Hemp Oil | 70 | 140 |
| Blend of Black Pepper Fruit and Clove Bud Oils | 3.75 | 7.5 |

Neuropathic pain results from conditions that compromise or abolish nerve function, such as multiple sclerosis, diabetes, nerve injury, or other conditions, and remains among the most challenging pain-related disorders to treat. Chronic inflammatory pain is a characteristic of several chronic diseases, including arthritis, inflammatory bowel disease, sickle-cell disease, etc., and represents another challenging clinical problem which faces many of the same treatment challenges as neuropathic pain. The composition of this invention may appear to promise the lessening of severe pain in these diseases. Therefore, this example demonstrates the potentiation effect of the invention on reducing inflammation and pain in mice model of inflammatory and neuropathic pain.

Example 2: In-Vivo Animal Models of Inflammatory and Neuropathic Pain

We used male CD-1 mice (9-10 weeks old; Charles River, Wilmington, MA, US) weighing 25-30 g upon arrival. They were randomly assigned to treatment groups and housed in ventilated plastic cages (4-5 per cage) in the animal facility of the University of California, Irvine. Animals were maintained in a pathogen-free environment (12-h light/dark cycle) under controlled temperature (20±2° C.) and humidity (55-60%) with food and water available ad libitum. Mice were allowed to acclimate for at least 7 days and experiments were conducted during the light phase of the light/dark cycle. All efforts were made to minimize the number of animals used and their discomfort. All procedures were approved by the Institutional Animal Care and Use Committee at the University of California, Irvine, and were carried out in strict accordance with the National Institutes of Health guidelines for the care and use of animals.

Test Compounds Preparation and Administration

HOE (code: VOHO-MGC) and PEA (batch No 20190604_03) were supplied by Metagenics Inc. The chemical composition of HOE is presented in Table A below. The extract was aliquoted upon arrival at our facility and kept at −80° C. until use. Before tests, aliquots were thawed at room temperature and the extract was diluted to the desired dose in a vehicle of 85% distilled water/15% Tween 80. Defrosted samples were discarded after use. HOE was subjected to an internal quality control to monitor its content of CBD and CBDA over time. The results are shown in Table B below. HOE, PEA and their combinations were administered in volumes of 10 mL/kg by oral gavage.

TABLE A

Chemical composition of hemp oil extract (HOE).

| Phytochemical | % g/g |
|---|---|
| Cannabidivarin (CBDV) | nd |
| Cannabidiolic acid (CBDA) | 1.43 |
| Cannabigerol (CBG) | nd |
| Cannabigerolic acid (CBGA) | 1.23 |
| Cannabidiol (CBD) | 9.34 |
| Tetrahydrocannabivarin (THCV) | nd |
| Delta-9-tetrahydrocannabinol (THC) | nd |
| Cannabichromene (CBC) | nd |
| Tetrahydrocannabinolic acid (THCA) | nd |
| Cannabichromenic acid (CBCA) | nd |
| Cannabielsoin (CBE) | 0.04 |
| Saturated fat | 9.3 |
| ω-9 fatty acids | 8.6 |
| ω-3 fatty acids | 21.1 |
| ω-6 fatty acids | 59.9 |

*where "nd" (Not detected) = less than 0.01% g/g.

TABLE B

Concentrations of cannabidiol (CBD) and cannabidiolic acid (CBDA) in HOE over time. Data are expressed as mean ± RSD of 4 serial dilutions, each dilution run in triplicates.

| Experiments | CBD %, g/g | CBDA %, g/g |
| --- | --- | --- |
| 1. | 2.98 ± 1.13 | 0.59 ± 0.64 |
| 2. | 2.97 ± 1.92 | 0.59 ± 1.40 |
| 3. | 3.33 ± 0.84 | 0.56 ± 2.93 |

Formalin Test

The formalin test was described in detail previously (e.g., see Dubuisson & Dennis, 1977). We injected formalin (1% v/v, 10 µL) or vehicle (saline, 10 µL) into the plantar surface of the right hind paw of male mice. Test compounds or vehicle (85% distilled water/15% Tween 80) were administered orally 1 h before formalin injection. Following injection, mice were immediately transferred to a transparent observation chamber where nocifensive behavior (time spent licking or biting the injected paw, number of shakings) was continuously recorded by a video camera for 60 min and then measured by trained observers blinded to experimental conditions. Behavioral tests and paw edema measurements were performed on post-formalin day (PFD) 7 in both the injected (ipsilateral) and contralateral paws.

Chronic Constriction Injury (CCI)

We elicited peripheral neuropathy in the left sciatic nerve of mice as described elsewhere (e.g., see Bennett & Xie, 1988). In brief, mice were anesthetized in 2-3% isoflurane in O2. Under aseptic conditions, the sciatic nerve was exposed at mid-thigh level through a small incision and loosely tied at 3 distinct sites (spaced at 1-mm interval) with 4-0 chromic catgut (Ethicon, USA). The wound was closed with a single muscle suture (Mersilk 5.0, Ethicon, USA) and glue to fasten the skin. Operated mice were returned to their home cages for recovery. Test compounds or vehicle were given by the oral route on day 7 after surgery (acute treatment) and then repeatedly once daily for 7 consecutive days (sub-chronic treatment). Behavioral tests were performed within 1 h of acute treatment or last subchronic treatment in both operated (ipsilateral) and contralateral paws. Mice were sacrificed by decapitation, the spinal cords were extruded by hydraulic pressure and processed for specific mRNA quantification in lumbar segments by real-time quantitative PCR.

Behavioral Testing

Mechanical sensitivity was assessed using a dynamic plantar aesthesiometer (Cat. No 37450, Ugo Basile, Italy). Mice were placed individually in transparent cages positioned on a wire mesh surface. After a 45-min habituation period, a mechanical stimulus was delivered to the plantar surface of the hind paws through the metal grid by an automated steel filament exerting an increasing force ranging from 0 to 5 grams over 10 s. The force at which the mouse withdrawn its paw (withdrawal threshold, in grams) was measured automatically. Thermal sensitivity was measured using a Hargreaves plantar test apparatus (San Diego Instruments, Inc, CA, USA). Mice were individually placed in small enclosures with a glass floor. After a 45-min habituation period, the plantar surface of the hind paws was exposed to a beam of radiant heat (infrared heat intensity: 3.0) through the glass floor. The cut-off time was set at 15 s. The time taken to withdraw the paw from heat stimulus (withdrawal latency, in seconds) was measured automatically. Each paw was tested 3 times with a 2-min interval between stimuli and the mean paw withdrawal threshold and latency were calculated. Paw thickness was measured in both ipsilateral and contralateral paws using a digital caliper (Cat. No 06-664-16, Fisher scientific, USA). Paw edema was quantified as the difference (paw thickness, in mm) between the ipsilateral paw thickness and the contralateral counterpart.

Real-Time Quantitative PCR

We extracted total RNA from lumbar spinal cords (L3-L6) using TRIzol™ reagent (Thermo Fisher Scientific, Walthman, USA) and purified with the PureLink™ RNA Mini Kit (Invitrogen, Carlsbad, USA) as directed by the supplier. Prior to purification, samples were rendered genomic DNA-free by passing the isolated RNA extract through a gDNA Eliminator spin column (Qiagen, Germantown, USA). RNA concentration and purity were determined using the Nano-Drop 2000/2000-c spectrophotometer (Thermo Fisher Scientific, Walthman, USA). cDNA was synthesized using 2 µg of total RNA as input for the High-Capacity cDNA RT Kit with RNase Inhibitor (Applied BioSystems, Foster City, USA) with a final reaction volume of 20 µL. First-strand cDNA was amplified using TaqMan™ Universal PCR Master Mix (Thermo Fisher Scientific, Walthman, USA) following the manufacturer's instructions. Real-time PCR primers and fluorogenic probes were purchased from Applied Biosystems (TaqMan® Gene Expression Assays, Foster City, CA). We used TaqMan gene expression assays for mouse Actin-$\beta$ (Mm00607939_s1), Hprt (Mm00446968_m1), Gapdh (Mm99999915_g1), Tnf-$\alpha$ (Mm00443258_m1), IL-1$\beta$ (Mm00434228_m1), IL-6 (Mm00446190_m1), and IL-10 (Mm00439614_m1) (Applied Biosystems, Foster City, CA). Real-time PCR reactions were performed in 96-well plates using CFX96™ Real-Time System (Bio-Rad, USA). The thermal cycling conditions were as follows: initial denaturation set at 95° C. for 10 min, followed by 45 cycles, where each cycle was performed at 95° C. for 30 s and at 55° C. for 60 s. The Bestkeeper software was used to determine the expression stability and the geometric mean of three different housekeeping genes (Actb, Hprt and Gapdh). $\Delta$Ct values were calculated as the difference between the Ct value of the geometric mean of these housekeeping genes and the Ct value of the genes of interest. The relative quantity of genes of interest was calculated by the 2-$\Delta\Delta$Ct method and expressed as fold change over vehicle control.

Pharmacokinetic Experiments

We administered HOE (100 mg-kg-1), PEA (10 or 20 mg-kg-1) or the combinations of both to adult mice in volumes of 10 mL-kg-1 by the oral route. The animals were deeply anesthetized with isoflurane at various time points following test compounds administration (0, 15, 30, 45 and 60 min), blood was collected by cardiac puncture into ethylenediamine-tetraacetic acid (EDTA)-rinsed syringes and transferred into 1 mL polypropylene plastic tubes containing spray-coated potassium-EDTA (K2-EDTA). Plasma was prepared by centrifugation at 1450×g at 4° C. for 15 min, and transferred into polypropylene tubes, which were immediately frozen and stored at −80° C. Animals were euthanized by decapitation, their spinal cords were quickly extruded by hydraulic pressure on an ice-cold glass plate and lumbar segments were harvested, frozen on dry ice and stored 80° C. until analyses.

Extraction of PEA, Anandamide (AEA) and 2-arachidonoyl-sn-glycerol (2-AG)

Extraction method was described elsewhere (e.g., see Astarita & Piomelli, 2009; Lin et al., 2012). Plasma (50 μL) was transferred into 8-mL glass vials and diluted with water (0.9 mL) and 50 μL of the following internal standards (ISTD): [2H4]-PEA, [2H4]-AEA, and [2H5]-2-AG (100 nM each). Samples were loaded onto preconditioned Oasis HLB cartridges (Waters Corporation, Milford Massachusetts, USA) washed with methanol (100%) and water and eluted under vacuum (3-5 mmHg). The cartridges were rinsed with methanol (40%). Acetonitrile (1 mL) was added, and vacuum pressure was increased gradually to 10 mmHg to ensure maximal analyte recovery. Eluates were dried under nitrogen and reconstituted in 100 μL of acetonitrile. Samples were transferred to deactivated glass inserts (200 μL) and placed inside amber glass vials (2 mL; Agilent Technologies, Wilmington, DE). Lumbar spinal cords (~15 mg) were transferred into 2 mL Precellys soft tissue tubes (Bertin Instruments, France) and spiked with 50 μL of ISTD ([2H4]-PEA, [2H4]-AEA, and [2H5]-2-AG, 100 nM each) and ice-cold acetone (1 mL). Samples were homogenized at 4° C., 6000 rpm, 15 s/cycle for 2 cycles with 20 s pause in between. The supernatants were carefully transferred into 8-mL glass vials and dried under nitrogen. 3 mL of chloroform/methanol (2:1, v/v) and 1 mL of water were added to the samples, which were then stirred vigorously and centrifuged at 3000 rpm for 15 min at 4° C. The lower phases were collected, while upper phases were extracted again with chloroform (2 mL). Eluates were dried under nitrogen and reconstituted in 100 μL of acetonitrile. Samples were transferred to deactivated glass inserts (200 μL) and placed inside amber glass vials (2 mL).

CBD and CBDA Extraction

Extraction method was described previously (e.g., see Vozella et al., 2019). We weighed HOE (8-10 mg) in 8-mL glass vials, added 5 mL of ethanol and stirred vigorously. The samples were diluted 100-fold with methanol and the diluted solutions (0.5 mL) were spiked with 5 μL of [2H3]-CBD (5.0 μg/mL) and filtered through a 0.45 μm syringe filter (Agilent Technologies, Wilmington, DE) followed by serial dilutions in methanol directly into 200 μL glass inserts placed in 2.0 mL vials. Plasma (100 μL) was transferred into 8-mL glass vials and mixed with 50 μL of [2H3]-CBD (100 ng/mL). Proteins were precipitated by addition of 0.5 mL ice-cold acetonitrile containing 1% formic acid. Lumbar spinal cord samples (~15 mg) were transferred into 2 mL Precellys soft tissue tubes and spiked with 50 μL of [2H3]-CBD (100 ng/mL) and 1 mL of ice-cold acetonitrile containing 1% formic acid. Spinal cord samples were then homogenized as described above, and the supernatants were carefully transferred into 8-mL glass vials. Plasma and spinal cord supernatants were stirred vigorously and centrifuged at 3000 rpm for 15 min at 4° C. After centrifugation, the supernatants were loaded onto 1 mL Captiva EMR lipid cartridges (Agilent Technologies, USA) and eluted under vacuum (3-5 mmHg). Tissue pellets were rinsed with water/acetonitrile (1:4, v/v; 0.2 mL), stirred for 30 s, and centrifuged at 3000 rpm for 15 min at 4° C. The supernatants were collected, transferred onto EMR cartridges, eluted, and pooled with the first eluate. The cartridges were rinsed with water/acetonitrile (1:4, v/v; 0.2 mL). Eluates were dried under a nitrogen and reconstituted in 100 μL of methanol containing 0.1% formic acid. Samples were transferred to deactivated glass inserts (200 μL) and placed inside amber glass vials (2 mL).

Liquid Chromatography/Tandem Mass Spectrometry (LC-MS/MS) Analysis

LC separations were carried out using a 1260 series LC system (Agilent Technologies, Santa Clara, CA), consisting of a binary pump with degasser, thermostated autosampler and column compartment coupled to a 6460C triple-quadrupole mass spectrometric detector (MSD; Agilent Technologies, Santa Clara, CA). Analytes were separated on an Eclipse XDB C18 column (1.8 μm, 2.1×30.0 or 50.0 mm; Agilent Technologies, Wilmington, DE). For CBD and CBDA analyses, the mobile phase consisted of water containing 0.1% formic acid as solvent A and methanol containing 0.1% formic acid as solvent B (e.g., see Vozella et al., 2019). Representative LC-MS/MS tracings are illustrated in Supplementary FIGS. 1-3. For PEA, AEA and 2-AG analyses, the mobile phase consisted of water containing 0.25% acetic acid and 5 mM ammonium acetate as solvent A and methanol containing 0.25% acetic acid and 5 mM ammonium acetate as solvent B (e.g., see Astarita & Piomelli, 2009). The flow rate was 0.3-0.5 mL/min. The step-gradient conditions were as follows. CBD and CBDA: starting at 72% B for 1.50 min, changed to 95% B at 1.51 min, and maintained till 2.5 min to remove any strongly retained materials from the column; the column was re-equilibrated for 3.5-5 min to 72% B before the next injection. PEA, AEA and 2-AG: starting at 78% B to 28% B in 8.00 min, changed to 95% B at 8.01 min, and maintained till 10.00 min; then changed back to 78% B at 10.01 min; the equilibration time was 5 min. The column temperature was maintained at 40° C. and the autosampler at 9° C. The total analysis time, including re-equilibration, was 6.0-15.0 min. The injection volume was 2.0 μL. To prevent carry over, the needle was washed in the autosampler port for 30 s before each injection, using a wash solution consisting of 10% acetone in water/methanol/isopropanol/acetonitrile (1:1:1:1, v/v). The MSD was operated in the positive electrospray ionization (ESI) mode, and analytes were quantified by multiple reaction monitoring (MRM), the acquisition parameters are given in Supplementary Table 1 (see Mabou Tagne, Alex & Fotio, Yannick & Lin, Lin & Squire, Erica & Ahmed, Faizy & Rashid, Tarif & Karimian, Elnaz & Piomelli, Daniele. (2021). *Palmitoylethanolamide and hemp oil extract exert synergistic anti-nociceptive effects in mouse models of acute and chronic pain*. Pharmacological Research. 167. 105545. 10.1016/j.phrs.2021.105545.). The capillary and nozzle voltages were 3500 V and 300-500 V, respectively. The drying gas temperature was 300-350° C. with a flow of 9.0-11.0 L/min. Sheath gas temperature was 300-375° C. with a flow of 12 L/min. Nebulizer pressure was set at 45-50 psi. The MassHunter software (Agilent Technologies, Santa Clara, CA) was used for instrument control, data acquisition and analysis.

Statistical Analysis

Results are presented as mean S.E.M. of n experiments. ED50 values were determined by linear regression analysis of dose-response curves. Individual slopes of the dose-response curves were compared by Student's t-test, according to the test of parallelism. Analyses were conducted using Prism software (GraphPad Software, San Diego, CA, Version 8.4.2). Areas under the time-course curves (AUC) were calculated using the trapezoidal rule. Differences between groups were determined by one- or two-way analysis of variance (ANOVA) followed by Dunnett's test for multiple comparisons, as appropriate. The significance level was set at P<0.05.

Antinociceptive Effects of HOE

To assess the antinociceptive effects of HOE, we first used the formalin test as a model of injury-induced spontaneous pain (e.g., see Dubuisson & Dennis, 1977). A single dose of the extract (10, 50 and 100 mg-kg-1) was given orally to male mice 1 h before intraplantar injection of formalin. As expected (e.g., see Dubuisson & Dennis, 1977), the chemical irritant produced an immediate nocifensive response consisting of two temporally distinct phases of licking and flinching of the injected limb (FIGS. 1, A and B; phase I: 0-10 min; phase II: 15-60 min). On post formalin day (PFD) 7, the acute pain event gave way to edema in the injected paw (FIG. 1, C) and hypersensitivity in both ipsilateral and contralateral paws (FIGS. 1, D and E).

Figure 1:
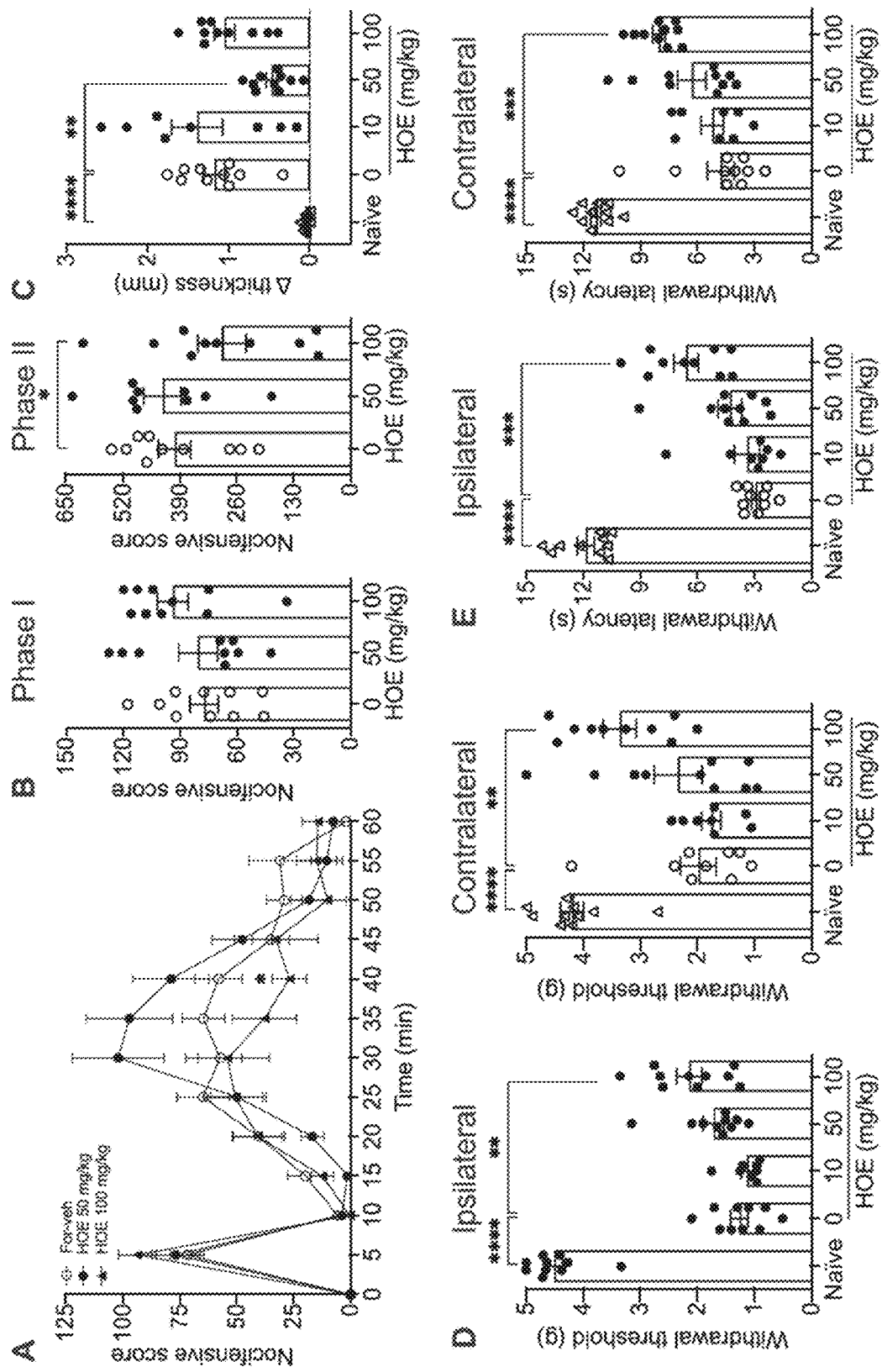
FIG. 1 illustrates effects of a single dose of hemp oil extract (HOE) on formalin-evoked acute and persistent nociceptive behaviors. (A) Time-course of the acute nocifensive response to formalin (1%, v/v). (B) Cumulative score of the phase I and phase II of the acute nocifensive response. (C) Paw thickness (injected paw thickness minus non-injected, in mm) at PFD7. (D) Formalin-evoked mechanical allodynia and (E) heat hyperalgesia to both ipsilateral and contralateral paws at PDF7. Data are expressed as mean±S.E.M. (n=8-10 per group) and analyzed by two-way (A and B) or one-way (C, D and E) ANOVA followed by Dunnett's test for multiple comparisons. $*P<0.05$, $P<0.01$, $*P<0.001$ and $****P<0.0001$ vs. Sham or Vehicle controls.

The results show that HOE (100 mg-kg-1) administration had no effect on the nocifensive score in Phase I, but reduced Phase II behavior by 27% (P<0.05 vs. vehicle) (FIG. 1, A-B). On PDF7, mechanical allodynia was also attenuated by 27% (P<0.01 vs. vehicle) and 62% (P<0.01 vs. vehicle), respectively, in ipsilateral and contralateral paws of mice that had received HOE (100 mg-kg-1) (FIG. 1, D). Heat hyperalgesia was alleviated by 41% (P<0.001 vs. vehicle) and 50% (P<0.001 vs. vehicle) in ipsilateral and contralateral paws, respectively (FIG. 1, E). Moreover, HOE reduced paw edema by 63% at 50 mg-kg-1 (P<0.01 vs. vehicle) but had no such effect at 100 mg-kg-1 (P>0.05 vs. vehicle) (FIG. 1, C).

Figure 2:
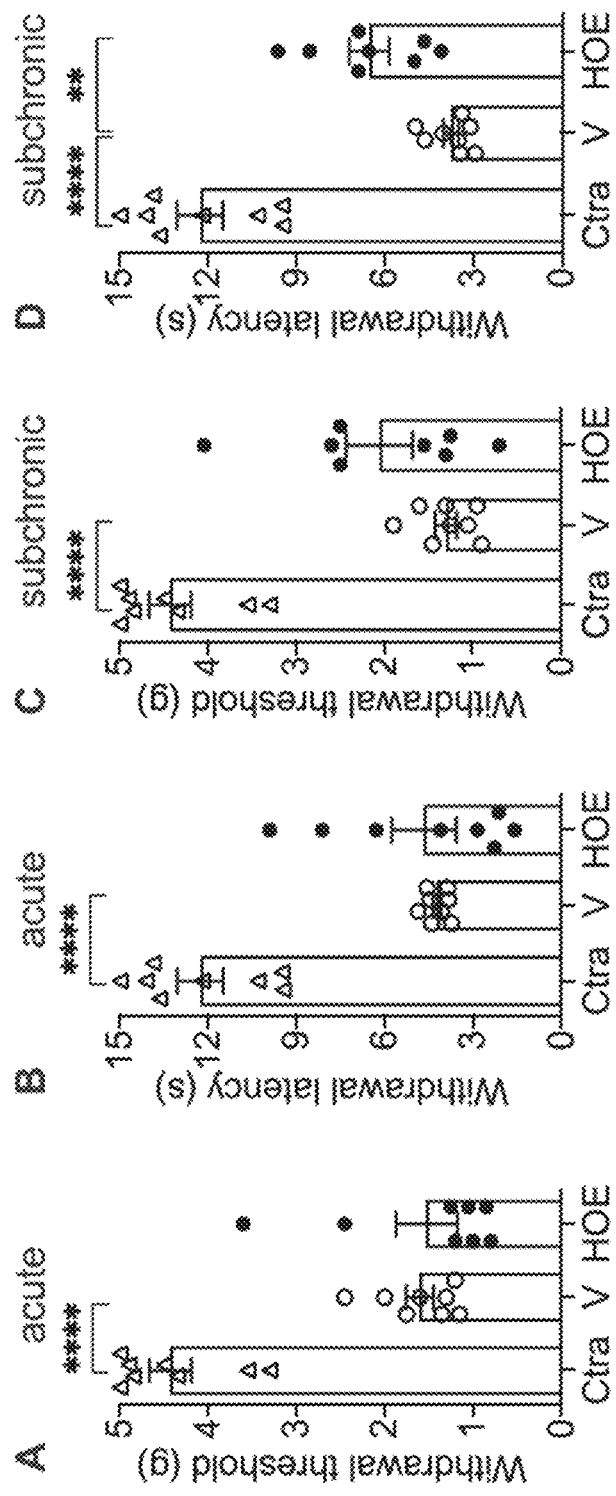
FIG. 2 illustrates effects of HOE on CCI-evoked mechanical allodynia (A and C) and heat hyperalgesia (B and D). A single dose of HOE (100 mg·kg-1) was administered orally to neuropathic mice on day 7 after CCI surgery (acute) and then repeatedly for 7 consecutive days (subchronic). (A and B) Mechanical allodynia and heat hyperalgesia on day 7 after CCI surgery. (C and D) Mechanical allodynia and heat hyperalgesia on day 14 after CCI surgery. Data are expressed as mean±S.E.M. (n=8 per group) and analyzed by oneway ANOVA followed by Dunnett's test for multiple comparisons. $P<0.01$ vs. Vehicle (V) and $**P<0.0001$ vs. Contralateral (Ctra; from vehicle-treated mice) controls.

Next, we produced peripheral neuropathy in mice by ligating their right sciatic nerve, which resulted in the development of mechanical allodynia and heat hyperalgesia in the operated limb (FIG. 2). On day 7 after surgery, we administered HOE by the oral route 1 h before testing. The results show that administration of a single dose of HOE (100 mg-kg-1) had no effect on either heat hyperalgesia or mechanical allodynia (FIGS. 2, A and B; P>0.05 vs. vehicle), whereas a 7-day treatment with the extract (100 mg-kg-1) decreased heat hyperalgesia by 33% (FIGS. 2, C and D; P<0.01 vs vehicle).

Antinociceptive Effects of PEA

Figure 3:
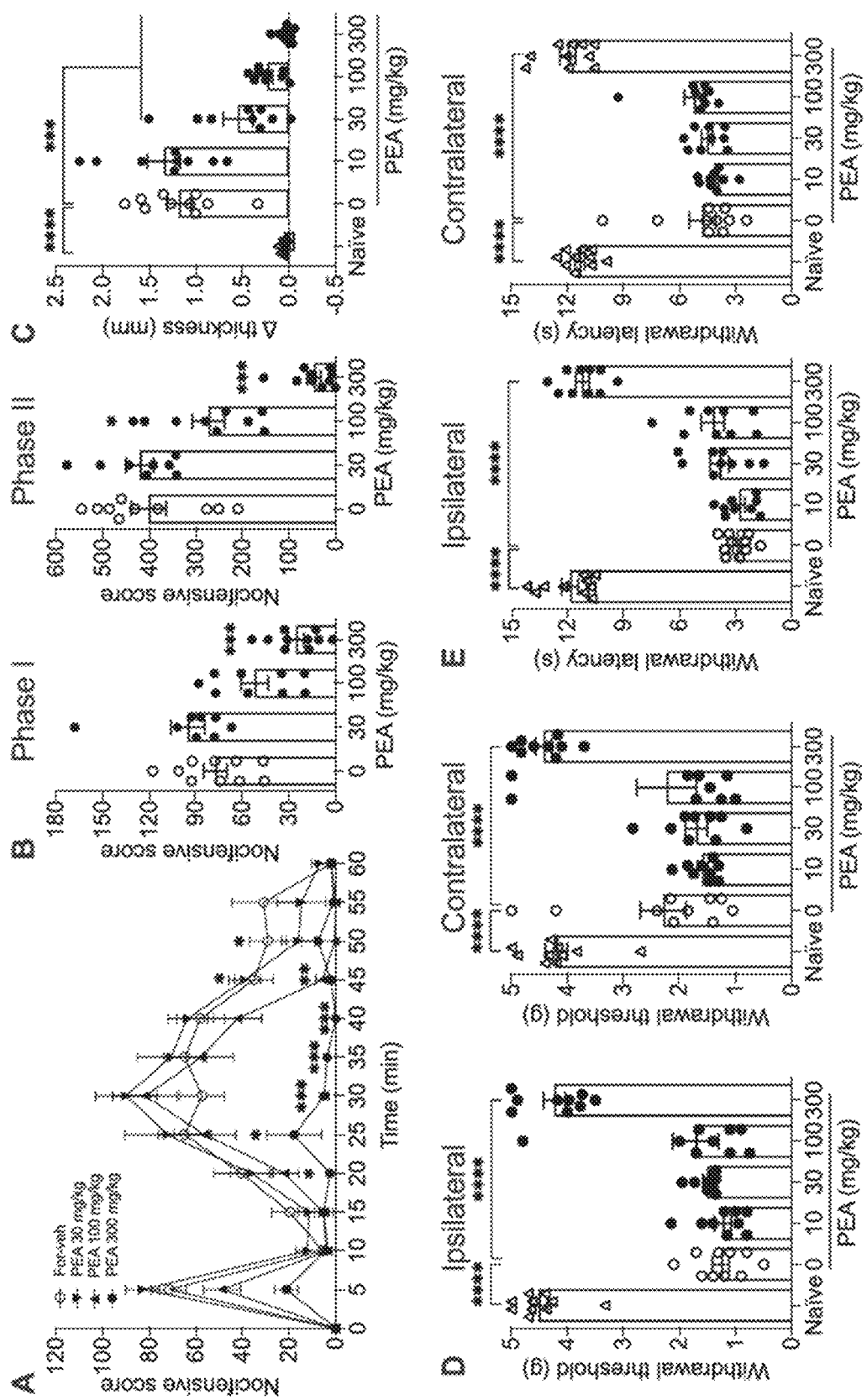
FIG. 3 illustrates effects of a single dose of PEA on formalin-evoked acute and persistent nociceptive behaviors. (A) Time-course of the acute nocifensive response to 1% formalin. (B) Cumulative score of the phase I and phase II of the acute nocifensive response. (C) Paw thickness (injected paw thickness minus non injected, in mm) at PFD7. (D) Mechanical and (E) heat sensitivities to both ipsilateral and contralateral paws at PDF7. Data are expressed as mean±S.E.M. (n=8-12 per group) and analyzed by two-way (A and B) or one-way ANOVA (C, D and E) followed by Dunnett's test for multiple comparisons. $*P<0.05$, $P<0.01$, $*P<0.001$ and $****P<0.0001$ vs. Sham or Vehicle controls.

As expected from previous work (e.g., see Calignano et al., 1998; LoVerme et al., 2006), administration of PEA (10, 30, 100 and 300 mg-kg-1, oral) resulted in a dose-dependent suppression of formalin-evoked nocifensive (FIG. 3, A-B) and inflammatory (FIG. 3C) responses. Mechanical allodynia on PFD7 was also attenuated by 91% (P<0.0001 vs. vehicle) and 112% (P<0.0001 vs. vehicle), respectively in ipsilateral and contralateral paws of mice that had received the highest dose of PEA (300 mg-kg-1) (FIG. 3, D). A similar effect was seen with heat hyperalgesia, which was alleviated by 93% (P<0.0001 vs. vehicle) and 110% (P<0.0001 vs. vehicle) in ipsilateral and contralateral paws, respectively (FIG. 3, E). At dosages lower than 300 mg-kg-1, PEA had no effect on either mechanical allodynia or heat hyperalgesia (P>0.05 vs. vehicle).

Figure 4:
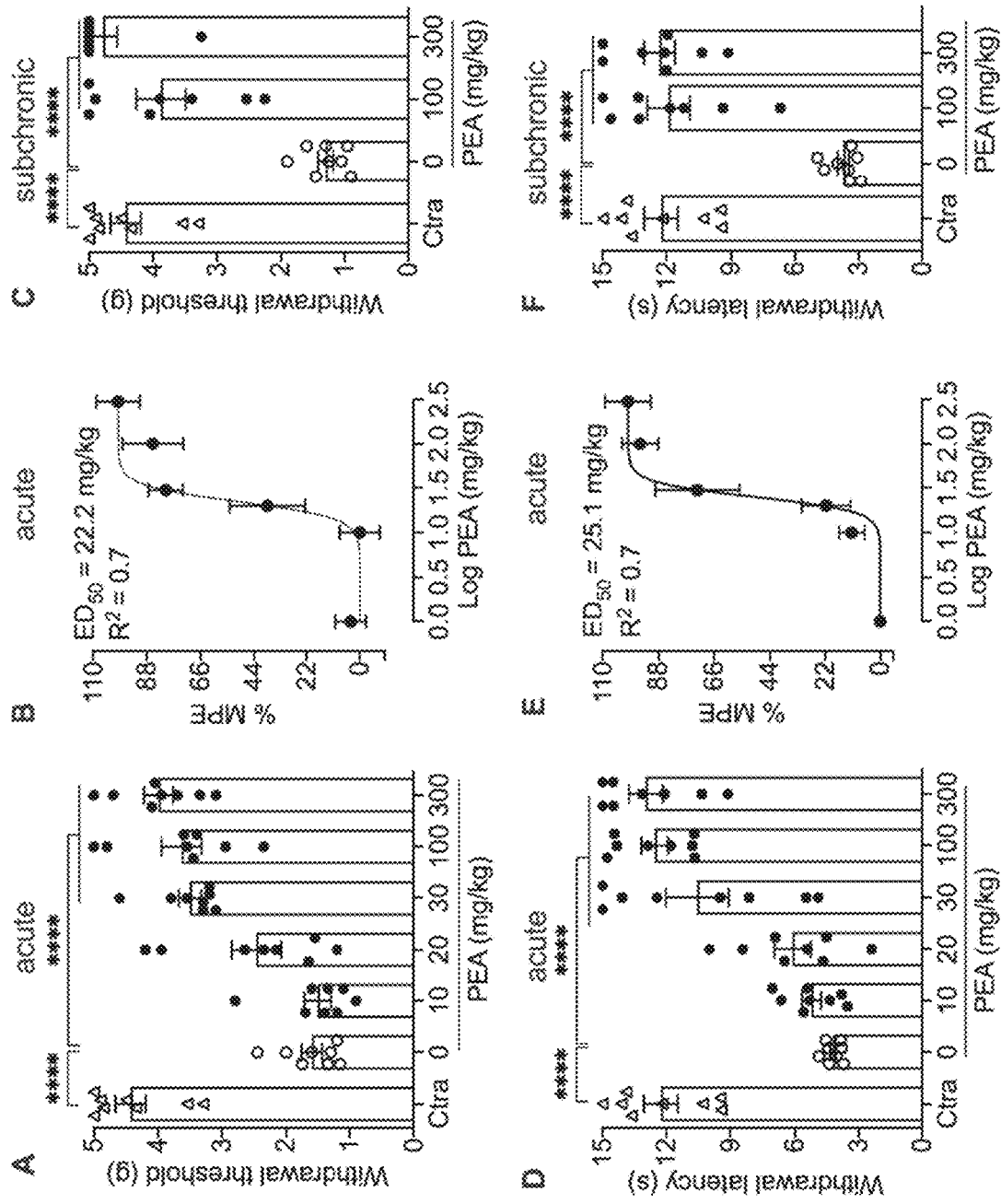
FIG. 4 illustrates effects of PEA on CCI-evoked mechanical allodynia (A-C) and heat hyperalgesia (D-F). PEA was administered orally to neuropathic mice on day 7 after CCI surgery (acute) and then repeatedly for 7 consecutive days (subchronic). Dose-response curves for the effects of PEA on CCI-induced mechanical allodynia (A, B) and heat hyperalgesia (D, E) on day 7 after surgery. Effects of subchronic administration of PEA (100 and 300 mg·kg-1) on CCI-induced mechanical allodynia (C) and heat hyperalgesia (F) on day 14 after surgery. Data are expressed as mean±S.E.M. (n=8 per group) and analyzed by one-way ANOVA followed by Dunnett's test for multiple comparisons. $P<0.01$ vs. Vehicle (V) and $**P<0.0001$ vs. Contralateral (Ctra) controls. % MPE, % maximal possible effect.

In the CCI model, a single PEA administration produced strong dose-dependent suppression of mechanical allodynia (ED50=22.2 mg-kg-1; 95% confidence interval [CI] ranging from 18.7 to 26.0 mg-kg-1; FIGS. 4, A and B) and heat hyperalgesia (ED50=25.1 mg-kg-1; 95% CI ranging from 21.8 to 29.1 mg-kg-1; FIGS. 4, D and E) by up to 85% (P<0.0001 vs. vehicle) and 109% (P<0.0001 vs. vehicle), respectively.

The two highest doses of PEA (100 or 300 mg-kg-1) were administered orally to neuropathic mice once daily for 7 consecutive days. The treatment reversed mechanical allodynia (FIG. 4, C) and heat hyperalgesia (FIG. 4, F), supporting prior studies indicating that there is no tolerance to the antinociceptive effects of PEA (LoVerme et al., 2006).

Antinociceptive Effects of Combinations of HOE and PEA

Figure 5:
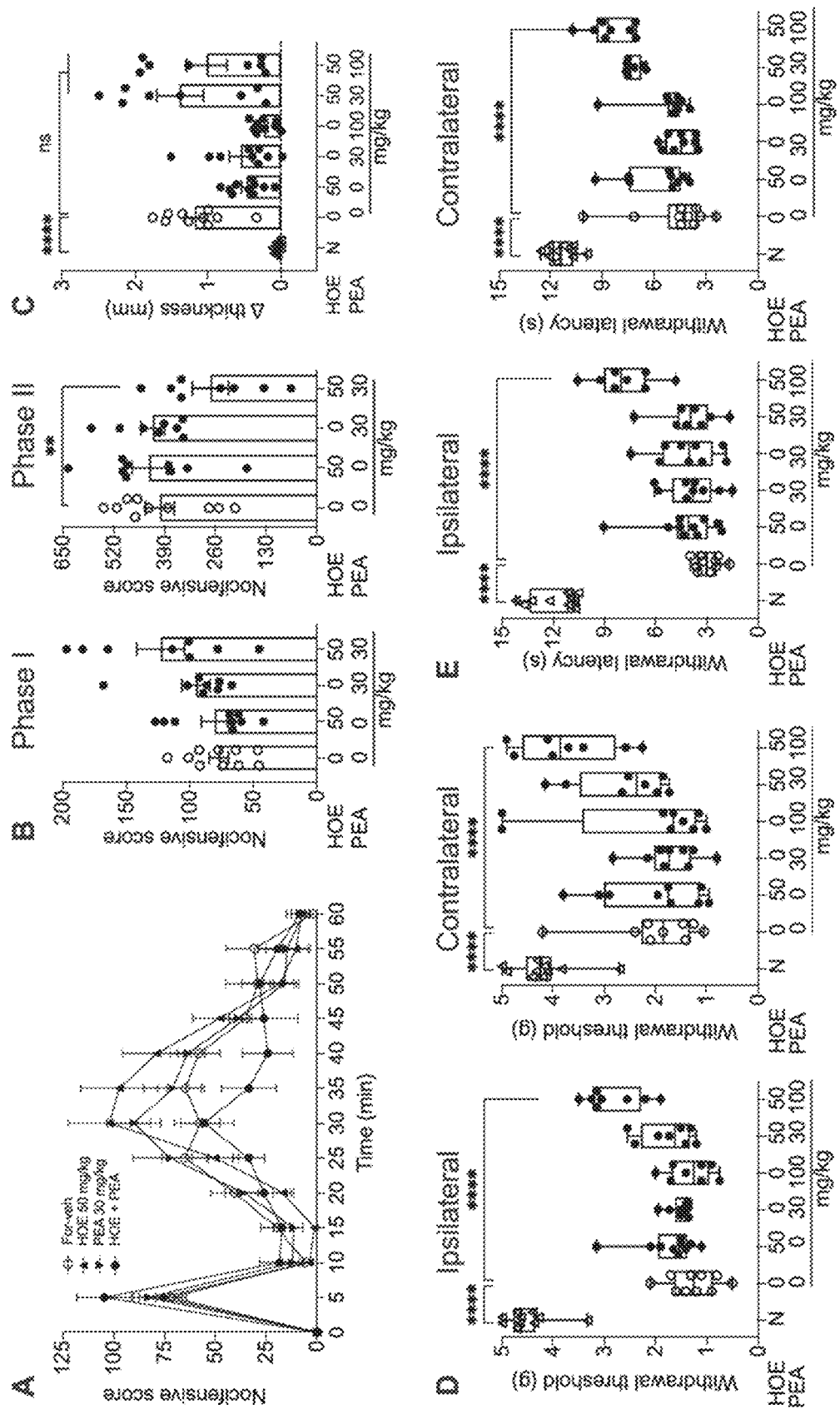
FIG. 5 illustrates effects of combinations of HOE with PEA on formalin-evoked acute and persistent nociceptive behaviors. (A) Time-course of the acute nocifensive response to 1% formalin. (B) Cumulative score of the phase I and phase II of the acute nocifensive response. (C) Paw thickness (injected paw thickness minus non injected, in mm) at PFD7. (D) Mechanical and (E) heat sensitivities to both ipsilateral and contralateral paws at PDF7. Data are expressed as mean±S.E.M. (n=8-10 per group) and analyzed by two-way (A and B) or one-way ANOVA followed by Dunnett's (C, D and E) test for multiple comparisons. $*P<0.05$, $P<0.01$, $*P<0.001$ and $****P<0.0001$. N: naïve; ns: nonsignificant.

Next, we tested whether HOE and PEA might interact when given in combination. Our results did not allow us to determine a median effective dose for HOE in either of the two experimental pain models, which made it impossible to evaluate the pharmacodynamic interactions between PEA and HOE by isobolographic analysis. Instead, we opted for a combination subthresholding approach which is a valid, effect-based strategy to investigate the biological activity of combinations of two or more compounds (e.g., see Foucquier & Guedj, 2015). We administered combinations of sub-effective oral doses of HOE (50 mg-kg-1) and PEA (30 or 100 mg-kg-1) 1 h before formalin (1% v/v). The results show that the HOE (50 mg-kg-1) and PEA (30 mg-kg-1) combination did not affect Phase I of formalin-evoked nocifensive behavior but reduced Phase II by 32% (P<0.01 vs. vehicle) (FIGS. 5, A and B). There was no effect on paw edema (FIG. 5, C).

On PFD7, formalin-evoked mechanical allodynia was attenuated by 49% (P<0.0001 vs. vehicle) and 75% (P<0.0001 vs. vehicle) respectively, in the ipsilateral and contralateral paws of mice that had received HOE (50 mg-kg-1) plus PEA (100 mg·kg-1) (FIG. 5, D). Likewise, heat hyperalgesia was decreased by 54% (P<0.0001 vs. vehicle) and 57% (P<0.0001 vs. vehicle), respectively, in the ipsilateral and contralateral paws (FIG. 5, E).

Figure 6:
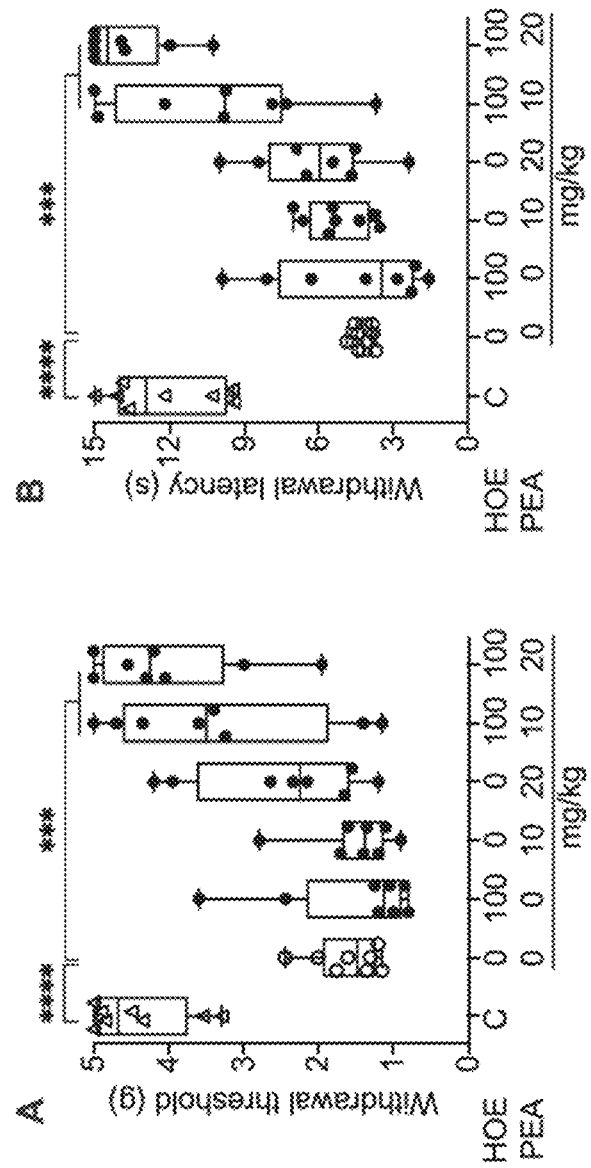
FIG. 6 illustrates effects of combinations of HOE with PEA on CCI-evoked mechanical allodynia (A) and heat hyperalgesia (B) to operated limbs. A single dose of HOE (100 mg·kg-1), alone or in combination with PEA (10 mg·kg-1) or PEA (20 mg·kg-1) was administered orally to neuropathic mice 1 h before testing. Data are expressed as mean±S.E.M. (n=8 per group) and analyzed by one-way ANOVA followed by Dunnett's test for multiple comparisons. $*P<0.05$, $P<0.01$, $*P<0.001$ and $****P<0.0001$. C, contralateral.

Finally, we asked whether the combination of HOE and PEA might affect hypersensitivity in the CCI model. We administered combinations of sub-effective oral doses of HOE (100 mg-kg-1) and PEA (10 or 20 mg-kg-1). FIG. 6 shows that the combinations reduced mechanical allodynia (FIG. 6, A) and heat hyperalgesia (FIG. 6, B) in the operated limbs by as much as 85% (P<0.001 vs. vehicle) and 118% (P<0.001 vs. vehicle), respectively.

RT qPCR Measurements

Figure 7:
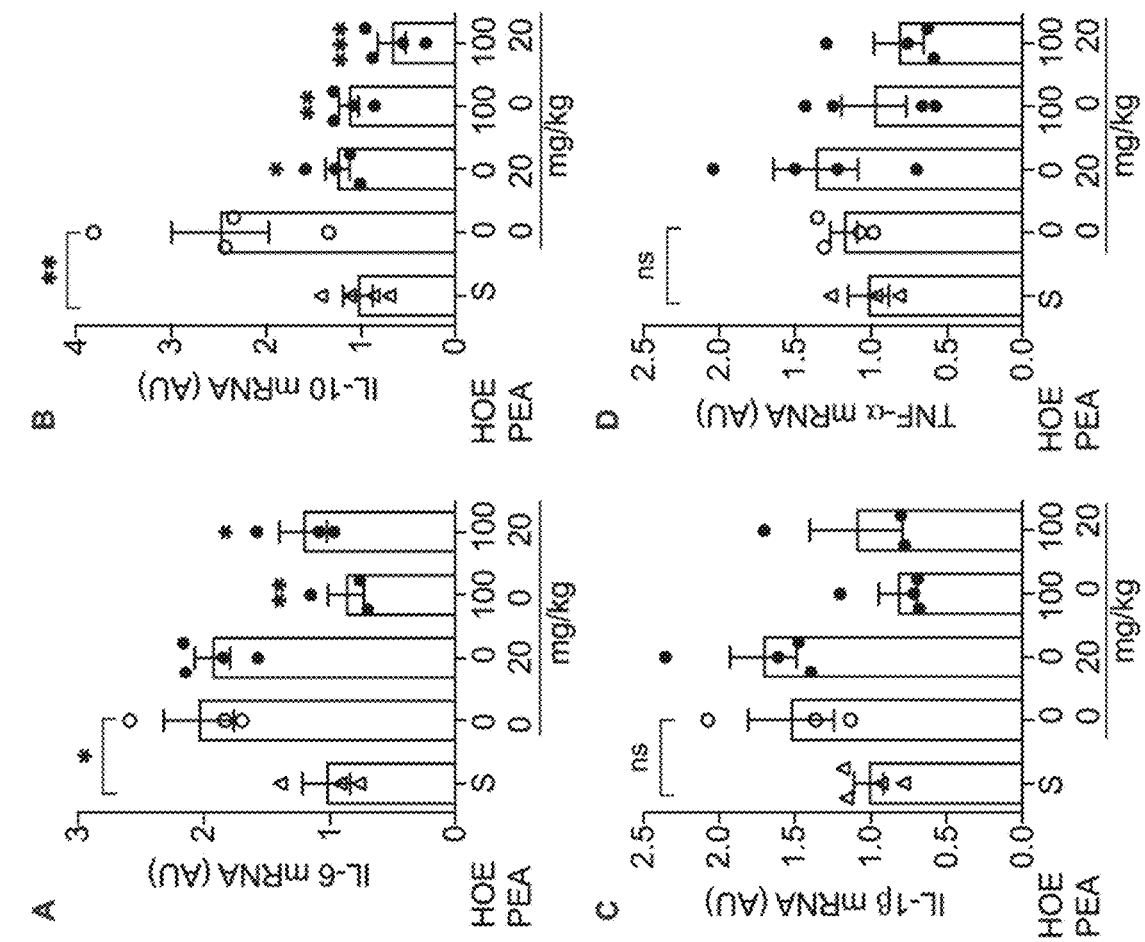
FIG. 7 illustrates effects of HOE (100 mg·kg-1), PEA (20 mg·kg-1) or their combination on mRNA levels (AU, Arbitrary Units) of IL-6 (A), IL-10 (B), IL-1b (C) and TNF-α (D) in lumbar spinal cords (L3-L6). Bars represent mean±S.E.M. (n=3-4 per group) and analyzed by oneway ANOVA followed by Dunnett's test for multiple comparisons. $*P<0.05$, $P<0.01$ and $*P<0.001$ vs. Vehicle. S, sham; ns, non-significant.

We examined whether HOE (100 mg-kg-1), PEA (20 mg-kg-1) or their combination might alter the transcription of proalgesic and inflammatory cytokines in lumbar spinal cords. The results show that CCI was associated with statistically detectable increases in IL-6 and IL-10 mRNA expression (FIGS. 7, A and B). IL-6 increased 2 folds (P<0.05 vs. sham) while IL-10 increased 2.5 folds (P<0.01 vs. sham). IL-1β mRNA levels were also increased but this trend failed to reach statistical significance (FIG. 7, C). By contrast, there were no statistically detectable changes in the expression of TNF-α mRNA (FIG. 7, D). Oral administration of a single dose of HOE (100 mg-kg-1) to neuropathic mice normalized IL-6 (P<0.01 vs. vehicle) and IL-10 (P<0.01 vs. vehicle) mRNA levels (FIGS. 7, A and B). When administered alone, PEA (20 mg-kg-1) halved IL-10 mRNA levels (P<0.05 vs. vehicle). The combination of HOE (100 mg-kg-1) and PEA (20 mg-kg-1) caused a 1.7-fold decrease in IL-6 mRNA expression (P<0.05 vs. vehicle), while lowering IL-10 mRNA levels 3.7 folds (P<0.001 vs. vehicle).

Pharmacokinetic Profiles of HOE, PEA or their Combination

Figure 8:
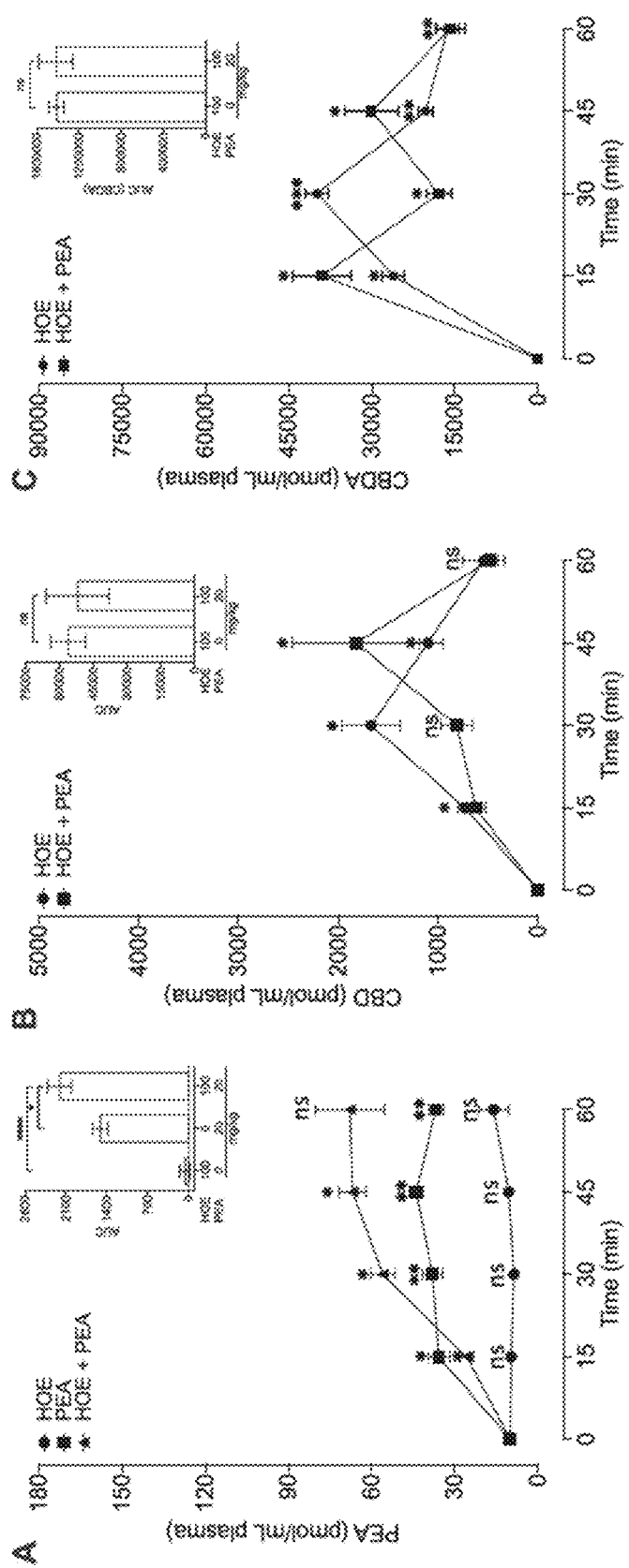
FIG. 8 illustrate concentration-time curves and overall drug exposure (AUC) for PEA (A), CBD (B) and CBDA (C) in mouse plasma, after oral administration of HOE (100 mg·kg-1) alone or in combination with PEA (20 mg·kg-1).

We measured the concentrations of PEA, CBD and CBDA in mouse plasma (FIG. 8) and spinal cord tissue (FIG. 9) in a 60-min period following oral administration of a single dose of the compounds or their combination. FIG. 8 shows concentration-time curves and overall exposure (area-under-the-curve, AUC) to PEA (A), CBD (B) and CBDA (C). Baseline levels of PEA were 10.03±0.4 pmolmL-1. Oral administration of HOE did not affect baseline PEA concentrations (FIG. 8, A). By contrast, plasma PEA levels increased rapidly by up to 44.1±2.4 pmol-mL-1 ($P<0.01$ vs. baseline) and 66.9±4.9 pmol-mL-1 ($P<0.05$ vs. baseline) after administration of PEA or the combination of HOE with PEA, respectively. Importantly, the combination of HOE with PEA (AUC=2,211±208 pmol-min-mL-1) resulted in greater exposure to PEA than HOE (AUC=72.1±83.9 pmol-min-mL-1; $P<0.0001$ vs HOE+PEA) and PEA (AUC=1,516±133.2 pmol-min-mL-1; $P<0.05$ vs HOE+PEA) given separately, suggesting that HOE enhances the bioavailability of PEA and prolongs its lifetime in circulation.

To assess whether PEA might affect the pharmacokinetic profile of HOE, we administered HOE, either alone or in combination with PEA, and measured plasma concentrations of two main components of HOE, CBD and CBDA. The results show that plasma CBD levels increased rapidly to 1,676±289.6 pmol-mL-1 ($P<0.05$ vs. baseline) and 1,826±635.6 pmol-mL-1 ($P<0.05$ vs. baseline) after administration of HOE or the combination of HOE with PEA, respectively (FIG. 8, B). Likewise, CBDA increased up to 39,917±2,042 pmol-mL-1 and 38,971±5,289 pmol-mL-1 after administration of HOE or the combination of HOE with PEA, respectively (FIG. 8, C). However, the combination of HOE with PEA [AUC (CBD)=52,153±13,999 pmol-min-mL-1; AUC (CBDA)=142,1014±162,688 pmol-min-mL-1] did not alter the overall exposure to CBD (FIG. 8, B) and CBDA (FIG. 8, C) compared to HOE alone [AUC (CBD)=56,334±7,757 pmol-min-mL-1; AUC (CBDA)=14,15702±70,988 pmol-min-mL-1], suggesting that PEA does not alter the pharmacokinetic properties of HOE.

FIG. 9 shows concentration-time curves and overall exposure to PEA (A), CBD (B) and CBDA (C) in mouse lumbar spinal cords. Baseline levels of PEA were 117.1±6.3 pmol-mg-1 of tissue (FIG. 9, A). Oral administration of HOE, PEA or their combination had no statistically detectable effect on such levels in the 60-min time frame of this study. This finding suggests that PEA does not readily enter the spinal cord and may exhibit its analgesic action mainly through a peripheral mechanism (e.g., see Calignano et al., 1998). By contrast, we were able to detect appreciable amounts of CBD and CBDA in spinal cord after oral administration of HOE alone or in combination with PEA (FIG. 9, B-C). Of note, oral administration of the combination of HOE with PEA [AUC (CBD)=29.21±7.36 pmol-min-mg-1; AUC (CBDA)=43.28±13.64 pmol-min-mg-1] did not statistically change the overall exposure of mice to CBD and CBDA compared with HOE alone [AUC (CBD)=36.3±5.78 pmol-min-mg-1; AUC (CBDA)=59.04±17.48 pmol-min-mg-1], suggesting that PEA does not affect the distribution of hemp in the spinal cord.

Effects of HOE Alone or in Combination with PEA on Endocannabinoid Levels

We measured the concentrations of the endocannabinoids AEA and 2-AG in mouse plasma and spinal cord tissue after oral administration of a single dose of HOE (100 mg-kg-1) alone or in combination with PEA (20 mg-kg-1). FIG. 10 shows that HOE alone or in combination with PEA did not affect plasma (FIGS. 10, A and B) or spinal cord (FIGS. 10, C and D) levels of the compounds ($P>0.05$ vs baseline) in the 60-min time frame of this study. These findings suggest that acute administration of HOE alone or in combination with PEA does not affect the endocannabinoid levels in mice.

Discussion

Legislative changes have increased the availability of products derived from industrial hemp (i.e., cannabis containing <0.3% $\Delta^{g}9$-THC), which are now widely used for self-medication of pain and other medical conditions (e.g., see Corroon & Phillips, 2018). Still very little is known, however, about the pharmacological properties of such products. In the present study, we set out to assess the efficacy of a full spectrum HOE, alone or in combination with PEA, in two complementary mouse models of pain, the formalin and CCI tests. We found that HOE has little or no effect when administered alone but synergizes with PEA to produce a greater-than-additive alleviation of pain-related behaviors. Pharmacokinetic studies suggest that one possible explanation for this synergistic interaction lies in the ability of HOE to prolong the exposure and lifetime of PEA in circulation.

Hemp contains a wide range of phytocannabinoids, terpenes, flavonoids and other bioactive molecules which likely contribute to its biological effects both individually and synergistically (e.g., see Russo, 2011). Identifying which of these myriad chemicals might be responsible for the modest antinociceptive properties of HOE would be a daunting task, but promising candidates include, among others, CBD and CBDA. For example, it has been shown that CBD produces antinociceptive effects in some animal models without causing apparent tolerance (e.g., see Britch et al., 2020; Costa et al., 2004, 2007; Genaro et al., 2017; Hammell et al., 2016; Malfait et al., 2000; Ward et al., 2014; Xiong et al., 2012). Likewise, studies have shown that CBDA exhibits antinociceptive and anti-inflammatory properties in rodents (e.g., see Rock et al., 2018; Zhu et al., 2020).

Cellular components of the immune system are thought to contribute to pain initiation and maintenance through the release of multiple cytokines (e.g., see Ren & Dubner, 2010; Scholz & Woolf, 2007; Thacker et al., 2007). The present results show that mRNA levels of IL-6 and IL-10 increased significantly in lumbar spinal cord tissue on day 7 after CCI surgery, an effect that was reduced by HOE alone or by the HOE/PEA combination. The increase in spinal IL-6 and IL-10 transcription is consistent with previous reports (e.g., see Austin & Moalem-Taylor, 2010; Duboq et al., 2013; Franchi et al., 2012; Sacerdote et al., 2013). The finding that CCI had little to no impact on IL-1 and TNF-α mRNAs is also in line with prior studies (e.g., see Curto-Reyes et al., 2015; Sacerdote et al., 2013; Simão da Silva et al., 2011). Oral administration of HOE either alone, or in combination with PEA caused a reduction in the mRNA expression of IL-6 and IL-10. This finding is relevant from a therapeutic perspective as the inhibition of IL-6 with neutralizing antibodies or other pharmacological tools has been found to alleviate nociceptive behaviors suggestive of neuropathic pain (e.g., see Arruda et al., 2000; Murakami et al., 2013).

It is believed that an important finding associated with the present invention is that one or more chemical constituents of hemp interact(s) with the endogenous analgesic and anti-inflammatory compound PEA to produce greater-than-additive antinociceptive effects. This synergism may be underpinned by pharmacodynamic and/or pharmacokinetic mechanisms. An antinociceptive synergism has been previously demonstrated between PEA and the endocannabinoid anandamide, which act via PPAR-α and CB1 cannabinoid receptors, respectively (e.g., see Russo et al., 2007). This mechanism is unlikely to be operational in our studies, however, because we found no evidence for enhanced endocannabinoid signaling after administration of the HOE/PEA combination, at least in plasma and spinal cord tissue at the time of measurement. While other pharmacodynamic interactions might have occurred, our results point to the possibility that the synergistic potentiation between HOE and PEA could have a pharmacokinetic underpinning. Indeed, we found that administering a combination of HOE and PEA enhances and prolongs the systemic exposure to PEA, compared to administering PEA alone. By contrast, PEA did not affect the pharmacokinetic properties of two quantitatively major constituents of HOE, CBD and CBDA. The mechanism underpinning the pharmacokinetic interaction between HOE and PEA is unknown, but two speculative scenarios are worth mentioning. First, HOE could act as a carrier to increase the intestinal absorption of PEA. This is sometimes observed with plant extracts, especially if they contain terpene compounds (e.g., see Williams & Barry, 2004). Second, HOE could slow down the liver degradation of PEA, which is primarily mediated by FAAH. Evidence in the literature suggests that CBD, which is present in HOE, inhibits FAAH activity at micromolar concentrations (e.g., see Leweke et al., 2012).

In conclusion, our findings identify an unexpected synergistic interaction between THC-free hemp and the endogenous analgesic and anti-inflammatory factor PEA, such that the combination of the two compounds exerts greater-than-additive antinociceptive effects in mouse models of acute and chronic pain. This synergism may be at least partially ascribed to the ability of HOE to increase the systemic exposure to PEA after oral administration.

Summary

Without being bound or limited by any particular theory, it is believed that the study associated with this particular example illustrates that:
1) HOE is modestly effective, when administered alone, in treating acute and chronic pain.
2) HOE synergizes with PEA to strongly enhance the pain relief and anti-inflammatory effects of PEA.
3) This synergism is partially supported by HOE extending the life of PEA in the blood circulation.

Additional aspects and findings of this study can be appreciated with reference to the following article: Mabou Tagne, Alex & Fotio, Yannick & Lin, Lin & Squire, Erica & Ahmed, Faizy & Rashid, Tarif & Karimian, Elnaz & Piomelli, Daniele. (2021). *Palmitoylethanolamide and hemp oil extract exert synergistic anti-nociceptive effects in mouse models of acute and chronic pain*. Pharmacological Research. 167. 105545. 10.1016/j.phrs.2021.105545.; the disclosure of which is incorporated herein by reference in its entirety.

Example 3: Human Subject Observation Study

Subjects with chronic inflammatory pain and or neuropathic pain were supplemented as follows:
600 mg PEA
500 mg Hemp Oil (containing 15 mg phytocannabinoids and 3 mg of terpenes)
a Formula with 40:1 of PEA and phytocannabinoids, respectively.

The following health-related quality of life and clinical symptom questionnaires were administered pre and post the intervention phases: Medical Outcomes Study 36 Item SF (e.g., see https://www.rand.org/health-care/surveys_tools/mos/36-item-short-form.html), PROMIS-43 Profile (e.g., see http://www.healthmeasures.net/explore-measurement-systems/promis/intro-to-promis), PROMIS-Global Health, PROMIS-Global Physical, PROMIS-Global Mental, PROMIS Pain Quality, PROMIS Physical Function, PROMIS Ability to Participate in Social Roles and Activities, PROMIS SF Sleep Disturbance, PROMIS SF Cognitive Function Abilities Subset, Fibromyalgia Impact Questionnaire (e.g., see Bennett R M. et al. Arthritis Res Ther. 2009; 11(4): R120), Brief Pain Inventory (e.g., see http://www.nperc.org/files/news/briefpain_short.pdf), American Pain Association Quality of Life Scale (e.g., see https://www.theacpa.org/wp-content/uploads/2017/08/Life_Scale_3.pdf). Quantitative sensory testing was also performed to detect pan thresholds by applying stimuli to the skin in ascending and descending order of magnitude (e.g., see Bennett M. Pain. 2001 May; 92(1-2):147-57). The results of the testing are shown in Table 6 below.

Surprisingly, the PEA/hemp combination was seen to induce greater improvements across multiple quality of life and pain-related scales compared to supplementation with either hemp or PEA alone.

TABLE 6

Results of Quality of Life and Symptom Assessment

| | Treatments | | |
|---|---|---|---|
| | PEA | Hemp oil | Formula |
| Change in health-related quality of life: | + | + | ++ |

Proinflammatory cytokine serum levels such as IFN-γ, TNF-α, and IL-17 were measured by ELISA as described previously (e.g., see Orefice. N. S. et al. Neurotherapeutics. 2016 April; 13(2): 428-438). Both PEA and hemp oil are known anti-inflammatory bioactive compounds, and we observed that formula treatment induced a significant reduction in the serum levels of these proinflammatory cytokines in comparison to hemp or PEA alone treatments. Plasma endocannabinoids were also analyzed, and formula resulted in a greater rebalance of circulating endocannabinoids compared to either hemp or PEA treatment alone.

Example 4: In Vitro Study

Fatty-acid amide hydrolase activity was measured as described previously (e.g., see Petrosino S. et al. Front Pharmacol. 2017; 8: 308). These findings demonstrate that elevations in endocannabinoid signaling following combined administration of PEA and hemp oil could contribute to the observed anti-nociceptive and -inflammatory effects, thereby our invention offers a potentially powerful strategy for treating inflammatory- and neuropathic-pain syndromes. Modulation of ECS through hemp oil and PEA targeting endogenous cannabinoid regulating enzymes represent a promising therapeutic option for chronic pain and inflammation.

The invention described above, including its composition and use in therapy has been described above to assist the skilled artisan in clearly understanding the invention. Of course, while still within the scope of this invention reasonable variations can occur, such as changes in excipients, variations in levels, differing regimens of dosages, and the like. For example, there is nothing in this disclosure that prevents for example the interchanging of one long chain fatty acid in a carrier for another, of the substitution of one surfactant for another.

Additional Embodiments

The following additional embodiments are provided, the numbering of which is not to be construed as designating levels of importance. Moreover, it is to be understood that the embodiments recited below are provided in conjunction with and in addition to the embodiments described above, as well as those claimed further below. Thus, it is also to be understood that variations, combinations, and/or modifications of the embodiment(s) and/or features of the embodiment(s) may be within the scope of the present invention. Likewise, alternative embodiments that result from combining, integrating, and/or omitting features of the embodiment(s) described herein may also be within the scope of the present invention.

In particular, one embodiment (i.e., "embodiment 1") provides a synergistic composition of palmitoylethanolamide (PEA) and hemp oil, comprising from about 38% to about 43% by weight PEA and from about 31% to about 35% by weight hemp oil.

Embodiment 2 relates to the composition of embodiment 1, wherein PEA and hemp oil synergistically enhance their therapeutic effect.

Embodiment 3 relates to a method of using the composition of embodiment 1 or embodiment 2, comprising ingesting the composition in an amount of 600 mg PEA and 500 mg hemp oil.

Embodiment 4 relates to a method of using the composition of embodiment 1 or embodiment 2 for the treatment of stress, comprising ingesting the composition in an amount sufficient to effect treatment thereof.

Embodiment 5 relates to a method of using the composition of embodiment 1 or embodiment 2 for the treatment of pain, comprising ingesting the composition in an amount sufficient to effect treatment thereof.

Embodiment 6 relates to a method of using the composition of embodiment 1 or embodiment 2 for analgesia, comprising ingesting the composition in an amount sufficient to provide the desired effect.

Embodiment 7 relates to a method of using the composition of embodiment 1 or embodiment 2 for the treatment of inflammation, comprising ingesting the composition in an amount sufficient to effect treatment thereof.

Embodiment 8 relates to a method of using the composition of embodiment 1 or embodiment 2 for the treatment of neuropathy, comprising ingesting the composition in an amount sufficient to effect treatment thereof.

Embodiment 9 relates to a method of using the composition of embodiment 1 or embodiment 2 for the regulation of tissue endocannabinoid levels.

Embodiment 10 relates to a method of using the composition of embodiment 1 or embodiment 2 for the regulation of levels of tissue endocannabinoids involved in sensitivity to pain.

Embodiment 11 relates to a method of using the composition of embodiment 1 or embodiment 2 for the regulation of levels of tissue endocannabinoids involved in response to stress Embodiment 12 relates to a method of using the composition of embodiment 1 or embodiment 2 for the regulation of levels of tissue anandamide (AEA) and 2-arachidonolyglycerol (2-AG).

Embodiment 13 relates to a method of using the composition of embodiment 1 or embodiment 2 for the regulation of fatty acid amide hydrolase (FAAH)

Embodiment 14 relates to a method of using the composition of embodiment 1 or embodiment 2 for the modulation of self-reported quality of life measures.

Embodiment 15 relates to a method of using the composition of embodiment 1 or embodiment 2 for the regulation of the endocannabinoid system.

Each of the additional embodiments so defined may be combined with any other embodiment or aspect of the embodiments of the invention described herein. In particular, any feature indicated as being optional or advantageous may be combined with any other feature or features indicated as being optional or advantageous, and each aspect of embodiments of the composition are to be understood as being applicable to use in the embodiments of the methods of using the composition.

The present invention has been described herein in an illustrative manner, and it is to be understood that the terminology that has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned articles, applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention claimed is:

1. A composition for administration to a subject, the composition comprising a synergistic combination of:
   palmitoylethanolamide (PEA); and
   a hemp oil comprising a broad-spectrum hemp extract obtained from aerial parts of industrial hemp plants comprising a phytocannabinoid component comprising cannabidiol (CBD);
   wherein the PEA and the hemp oil are present in the composition in a weight ratio (wt./wt.) of from about 1.2:1 to about 4.5:1 (PEA:hemp oil), and
   wherein the composition is formulated for oral administration to the subject.

2. The composition of claim 1, wherein the combination of the PEA and the hemp oil is present in the composition in an amount effective to, upon administration of a serving of the composition to a subject:
   (i) regulate tissue endocannabinoid levels;
   (ii) inhibit or reduce nociception;
   (iii) induce or increase analgesia;
   (iv) inhibit or reduce inflammation;
   (v) improve a self-reported quality of life of the subject; or
   (vi) any combination of (i)-(v); of the subject.

3. The composition of claim 1, wherein the composition has a serving size with a total weight of from about 300 to about 1800 mg, and wherein the composition comprises:
   (i) from about 300 to about 700 mg, optionally from about 300 to about 600 mg, of the PEA;
   (ii) from about 70 to about 500 mg of the hemp oil; or
   (iii) both (i) and (ii); in a serving of the composition.

4. The composition of claim 1, wherein the composition comprises:
   (i) from about 300 to about 600 mg of the PEA; and
   (ii) from about 70 to about 500 mg of the hemp oil.

5. The composition of claim 3, wherein the PEA is present in an amount of from about 38 to about 43 weight percent (wt. %) and the hemp oil is present in amount of from about 31 to about 35 wt. %, each based on the total weight of the serving of the composition.

6. The composition of claim 1, wherein the hemp oil comprises
   a terpene component comprising at least one terpene.

7. The composition of claim 1, wherein the phytocannabinoid component:
   also comprises cannabigerol (CBG); and
   is present in an amount of at least 15 mg in a serving of the composition.

8. The composition of claim 1, wherein the composition comprises the PEA and the phytocannabinoid component (PCC) of the hemp oil in a weight ratio of from about 50:1 to about 30:1, optionally of about 40:1 (PEA:PCC).

9. The composition of claim 8, wherein the composition comprises the PEA and the PCC of the hemp oil in a weight ratio of about 40:1 (PEA:PCC).

10. The composition of claim 6, wherein the terpene component:
    (i) comprises β-caryophyllene (BCP);
    (ii) is present in an amount of at least 3 mg in a serving of the composition; or
    (iii) both (i) and (ii).

11. The composition of claim 1, wherein the composition is adapted for administration to the subject in a dosage form comprising a softgel or capsule shell encapsulating a dose of the combination of the PEA and the hemp oil, and wherein a serving of the composition comprises at least one dose, optionally at least two doses, of the softgel or capsule shell encapsulated combination.

12. The composition of claim 11, wherein the serving of the composition comprises at least two doses of the softgel or capsule shell encapsulated combination.

13. A method of ameliorating a condition of a subject comprising administering to the subject an effective amount of the composition of claim 1, wherein the condition of the subject is associated with:
    (i) pain;
    (ii) inflammation;
    (iii) stress;
    (iv) neuropathy; or
    (v) any combination of (i)-(iv); in the subject.

14. The method of claim 13, wherein the composition is administered to the subject in an amount effective to:
    (i) modulate the endocannabinoid system;
    (ii) regulate tissue endocannabinoid levels;
    (iii) inhibit or reduce nociception;
    (iv) induce or increase analgesia;
    (v) inhibit or reduce inflammation;
    (vi) improve self-reported quality of life; or
    (vii) any combination of (i)-(vi); of the subject.

15. The method of claim 13, wherein the method comprises administering the composition to the subject in an amount effective to modulate the endocannabinoid system of the subject, wherein modulating the endocannabinoid system of the subject comprises:
    (i) inhibiting the activity of fatty acid amide hydrolase (FAAH);
    (ii) reducing the expression of fatty acid amide hydrolase (FAAH); or
    (iii) both (i) and (ii); in the subject.

16. The method of claim 13, wherein the method comprises administering the composition to the subject in an amount effective to regulate tissue endocannabinoid levels of the subject, and wherein regulating tissue endocannabinoid levels comprises:

(i) increasing levels of anandamide (AEA);
(ii) increasing levels of 2-arachidonolyglycerol (2-AG); or
(iii) both (i) and (ii); in tissue of the subject.

17. The method of claim 13, wherein the composition is provided in a dosage form comprising a softgel or capsule shell encapsulating a dose of the combination comprising about 300 mg of the PEA and from about 70 to about 250 mg of the hemp oil, and wherein the method comprises orally administering at least one, optionally at least two, of the softgel or capsule shell encapsulated combination to the subject per day for at least two consecutive days.

18. The method of claim 17, wherein the method comprises orally administering at least two of the softgel or capsule shell encapsulated combination to the subject per day for at least two consecutive days.

19. The composition of claim 1, comprising:
about 300 mg of the PEA;
about 70 mg of the hemp oil; and
about 3.75 mg of a blend of black pepper fruit oil and clove bud oil;
wherein the composition is adapted for administration to the subject in a dosage form comprising a softgel encapsulating a dose of a combination of the PEA, the hemp oil, and the blend of black pepper fruit oil and clove bud oil, and
wherein a serving of the composition comprises at least one dose, optionally at least two doses, of the softgel.

* * * * *